US012239310B2

(12) United States Patent
Nader et al.

(10) Patent No.: US 12,239,310 B2
(45) Date of Patent: Mar. 4, 2025

(54) ORTHOPEDIC STABILIZATION DEVICE, KIT AND METHOD

(71) Applicant: Medline Industries, LP, Northfield, IL (US)

(72) Inventors: Samuel Nader, Arlington Heights, IL (US); Wesley Lloyd Reed, Libertyville, IL (US); Dinesh Koka, Winter Park, FL (US)

(73) Assignee: Medline Industries, LP, Northfield, IL (US)

( * ) Notice: Subject to any disclaimer, the term of this patent is extended or adjusted under 35 U.S.C. 154(b) by 431 days.

(21) Appl. No.: 17/730,709

(22) Filed: Apr. 27, 2022

(65) Prior Publication Data

US 2023/0346363 A1 Nov. 2, 2023

(51) Int. Cl.
*A61B 17/04* (2006.01)
(52) U.S. Cl.
CPC ...... *A61B 17/0401* (2013.01); *A61B 17/0487* (2013.01); *A61B 2017/0496* (2013.01)
(58) Field of Classification Search
CPC ............ A61B 17/0401; A61B 17/0487; A61B 2017/0496; A61B 17/8061; A61B 2017/0404; A61B 2017/0414; A61B 2017/0417; A61B 2017/0448; A61B 2017/0459
See application file for complete search history.

(56) References Cited

U.S. PATENT DOCUMENTS

| 4,750,492 A | 6/1988 | Jacobs |
| 5,306,301 A | 4/1994 | Graf |
| 5,709,686 A | 1/1998 | Talos |
| 5,921,986 A | 7/1999 | Bonutti |
| 6,110,207 A | 8/2000 | Eichhorn |
| 6,117,160 A | 9/2000 | Bonutti |
| 6,454,769 B2 | 9/2002 | Wagner |
| 6,517,578 B2 | 2/2003 | Hein |

(Continued)

FOREIGN PATENT DOCUMENTS

| DE | 4343117 | 6/1995 |
| WO | 2005018472 | 3/2005 |

OTHER PUBLICATIONS

"Dynamic and Load-to-Failure Testing of the DePuy Synthes FIBULINK® Syndesmosis Repair System and Arthrex Syndesmosis TightRope® XP Implant System"; DePuy Synthes Research and Development, 2020 (3 pgs.).

(Continued)

*Primary Examiner* — Kelly J Bekker
*Assistant Examiner* — Andrew P. Restaino
(74) *Attorney, Agent, or Firm* — Fitch, Even, Tabin & Flannery LLP

(57) ABSTRACT

An orthopedic stabilization device is provided having a first button, a second button and a suture extending therebetween. The first button has a base portion and a depending loop having an elongated loop opening therethrough. A locking member extends through the elongated loop opening and is retained with the loop when in a retained orientation and insertable or removable when in an unretained orientation. A portion of the suture is frictionally retainable between the locking member and the loop to thereby tie the first button to the second button when the locking member is in a clamping position.

20 Claims, 22 Drawing Sheets

(56) References Cited

U.S. PATENT DOCUMENTS

| | | |
|---|---|---|
| 6,635,072 B1 | 10/2003 | Ramamurti |
| 6,716,218 B2 | 4/2004 | Holmes |
| 6,821,278 B2 | 11/2004 | Frigg |
| 6,955,677 B2 | 10/2005 | Dahners |
| D520,637 S | 5/2006 | Kay |
| 7,309,340 B2 | 12/2007 | Fallin |
| 7,695,503 B1 | 4/2010 | Kaiser |
| 7,776,039 B2 | 8/2010 | Bernstein |
| 7,875,057 B2 | 1/2011 | Cook |
| 7,875,058 B2 | 1/2011 | Holmes, Jr. |
| 7,901,431 B2 | 3/2011 | Shurnas |
| 7,938,847 B2 | 5/2011 | Fanton |
| 7,955,364 B2 | 6/2011 | Ziolo |
| D648,027 S | 11/2011 | Vancelette |
| 8,133,258 B2 | 3/2012 | Foerster |
| 8,137,351 B2 | 3/2012 | Prandi |
| 8,206,446 B1 | 6/2012 | Montgomery |
| 8,216,242 B2 | 7/2012 | Marchyn |
| 8,231,654 B2 | 7/2012 | Kaiser |
| 8,313,492 B2 | 11/2012 | Wong |
| 8,343,196 B2 | 1/2013 | Schneider |
| 8,388,655 B2 | 3/2013 | Fallin |
| 8,529,608 B2 | 9/2013 | Terrill |
| 8,545,535 B2 | 10/2013 | Hirotsuka |
| 8,696,716 B2 | 4/2014 | Kartalian |
| 8,764,763 B2 | 7/2014 | Wong |
| 8,845,698 B2 | 9/2014 | Schneider |
| 8,852,245 B2 | 10/2014 | Schneider |
| 8,876,873 B2 | 11/2014 | Schneider |
| 8,906,076 B2 | 12/2014 | Mocanu |
| 8,940,026 B2 | 1/2015 | Hilse |
| 9,005,245 B2 | 4/2015 | Thornes |
| 9,011,540 B1 | 4/2015 | Castro |
| D740,943 S | 10/2015 | Neufeld |
| 9,259,217 B2 | 2/2016 | Fritzinger |
| 9,295,505 B2 | 3/2016 | Schneider |
| D756,844 S | 5/2016 | Almes |
| 9,351,776 B2 | 5/2016 | Terrill |
| D766,439 S | 9/2016 | Dacosta |
| 9,463,034 B2 | 10/2016 | Wong |
| 9,468,479 B2 | 10/2016 | Marotta |
| 9,486,264 B2 | 11/2016 | Reiley |
| 9,492,201 B2 | 11/2016 | Reiley |
| D780,922 S | 3/2017 | Dacosta |
| D780,926 S | 3/2017 | Dacosta |
| 9,662,157 B2 | 5/2017 | Schneider |
| 9,750,515 B2 | 9/2017 | Soliman |
| 9,763,716 B2 | 9/2017 | Terrill |
| 9,839,448 B2 | 12/2017 | Reckling |
| 9,936,983 B2 | 4/2018 | Mesiwala |
| 9,949,843 B2 | 4/2018 | Reiley |
| 10,010,321 B2 | 7/2018 | Cocaign |
| 10,022,138 B2 | 7/2018 | Wong |
| 10,130,358 B2 | 11/2018 | Palmer |
| 10,166,033 B2 | 1/2019 | Reiley |
| 10,201,427 B2 | 2/2019 | Mauldin |
| 10,206,670 B2 | 2/2019 | Thornes |
| 10,245,085 B2 | 4/2019 | Terrill |
| 10,245,086 B2 | 4/2019 | Treace |
| 10,245,088 B2 | 4/2019 | Dayton |
| 10,251,686 B2 | 4/2019 | Zajac |
| 10,292,745 B2 | 5/2019 | Palmer |
| 10,349,931 B2 | 7/2019 | Stone |
| 10,363,140 B2 | 7/2019 | Mauldin |
| 10,376,206 B2 | 8/2019 | Sand |
| D869,657 S | 12/2019 | Hollis |
| D891,619 S | 7/2020 | Hollis |
| 11,103,293 B2 | 8/2021 | Palmer |
| D932,012 S | 9/2021 | Dacosta |
| 11,109,855 B2 | 9/2021 | Shoshtaev |
| 11,266,451 B2 | 3/2022 | Hollis |
| 11,272,967 B2 | 3/2022 | Niver |
| 11,382,671 B2 | 7/2022 | Hayes |
| 11,426,154 B2 | 8/2022 | Niver |
| 11,602,383 B2 | 3/2023 | Palmer |
| 11,602,384 B2 | 3/2023 | Palmer |
| 2002/0161439 A1 | 10/2002 | Strobel |
| 2003/0236555 A1 | 12/2003 | Thornes |
| 2008/0051786 A1 | 2/2008 | Jensen |
| 2008/0208252 A1 | 8/2008 | Holmes |
| 2009/0210010 A1 | 8/2009 | Strnad |
| 2010/0268273 A1 | 10/2010 | Albertorio |
| 2011/0009866 A1 | 1/2011 | Johnson |
| 2012/0123484 A1 | 5/2012 | Lietz |
| 2013/0030480 A1 | 1/2013 | Donate |
| 2013/0035720 A1* | 2/2013 | Perriello ............... A61F 2/0811 606/232 |
| 2014/0257294 A1 | 9/2014 | Gédet |
| 2016/0310191 A1 | 10/2016 | Seykora |
| 2017/0156767 A1 | 6/2017 | Chaudot |
| 2018/0008255 A1* | 1/2018 | Fallin ................. A61B 17/885 |
| 2018/0249998 A1* | 9/2018 | Chavan ............ A61B 17/0401 |
| 2018/0280066 A1 | 10/2018 | O'Connor |
| 2020/0015871 A1 | 1/2020 | Niver |
| 2021/0068806 A1 | 3/2021 | Niver |
| 2021/0361333 A1 | 11/2021 | Palmer |
| 2022/0160408 A1 | 5/2022 | Hollis |
| 2022/0265330 A1 | 8/2022 | Niver |
| 2022/0296287 A1 | 9/2022 | Hollis |

OTHER PUBLICATIONS

"FIBULINK® Syndesmosis Repair System Surgical Technique"; DePuy Synthes, 2021 (19 pgs.).

"Load-to-Failure and Cyclic Displacement of the Arthrex Knotless TightRope Syndesmosis and Biomet ZipTight™ Ankle Syndesmosis"; Arthrex Research and Development, 2013 (1 pg.).

"Syndesmosis TightRope® XP Implant System Surgical Technique"; Arthrex, Inc.; 2019 (7 pgs.).

"ZipTight™ Ankle Syndesmosis Surgical Technique"; Zimmer Biomet, 2019 (10 pgs.).

Arthrex Inc., Knotless TightRope, 2012.

Arthrex Inc., Lisfranc TightRope Fixation, 2013.

Arthrex Inc., PushLock, Knotless Instability Repair, 2013.

Arthrex Inc., TightRope Syndesmosis Fixation, 2012.

Stryker, ReeIX STT, Knotless Anchor System, 2015.

Wright, Piton, 3.5mm Knotless Fixation Implant, Jun. 27, 2016.

Zimmer Biomet, JuggerLoc Bone-to-Bone System for Ankle Syndesmosis Fixation, 2017.

ACUMED, Ankle Plating System 3 Brochure, Jun. 2022 (60 pages).

OsteoMed, "ExtremiLock Foot Plating System," published prior to 2017.

Screenshots from Facebook, Wright Medical, https://www.facebook.com/WrightMedical/videos/charlotte-lisfranc-reconstruction-system-animation/1419857841359191/, Nov. 23, 2016, Retrieved Feb. 9, 2023.

Stryker, "Stryker Foot & Ankle Plating Systems," Operative Technique Anchorage 2 CP, 2016.

Wright Medlical, "Charlotte Lisfranc Reconstruction System" brochure, Sep. 16, 2016, 13 pages.

* cited by examiner

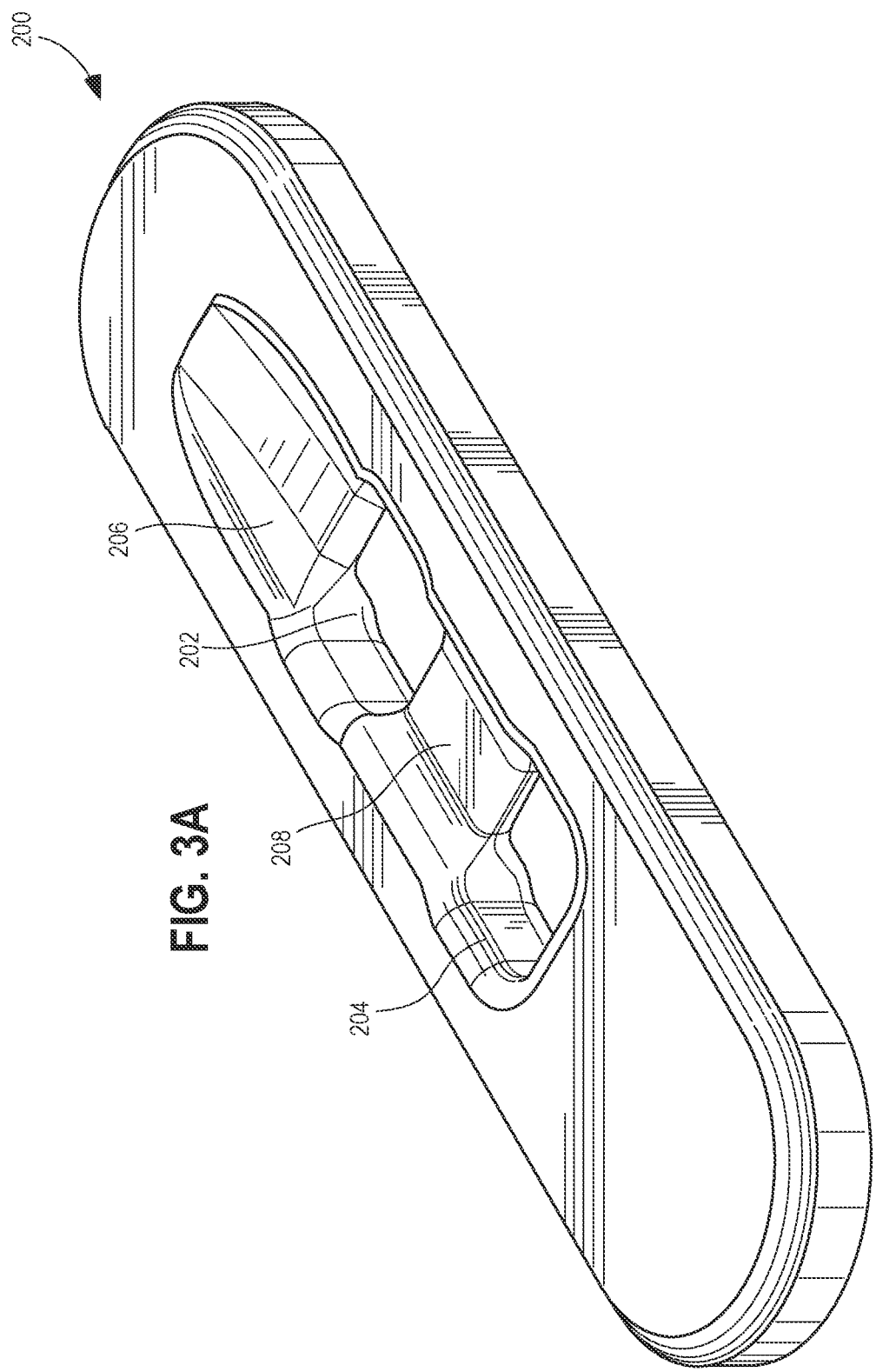

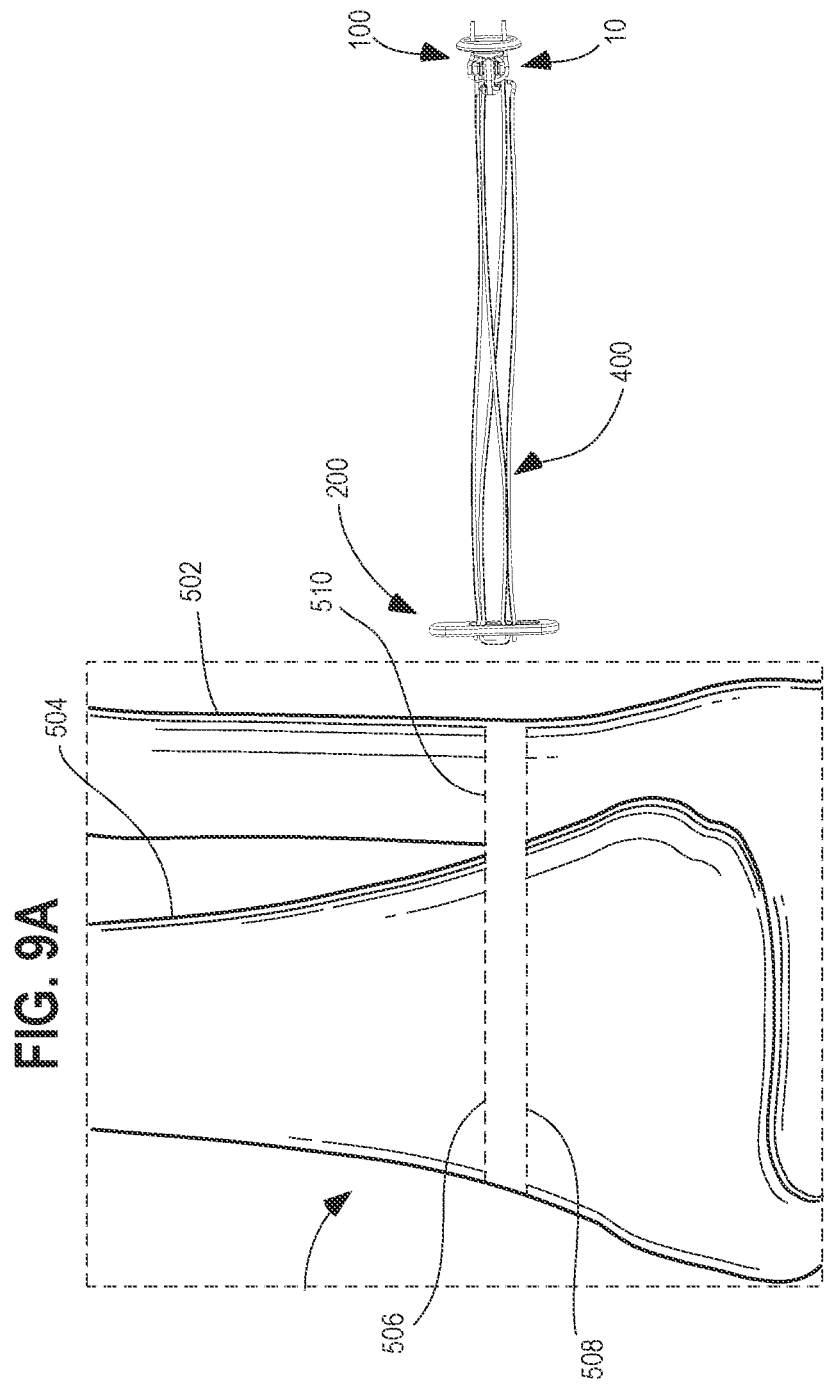

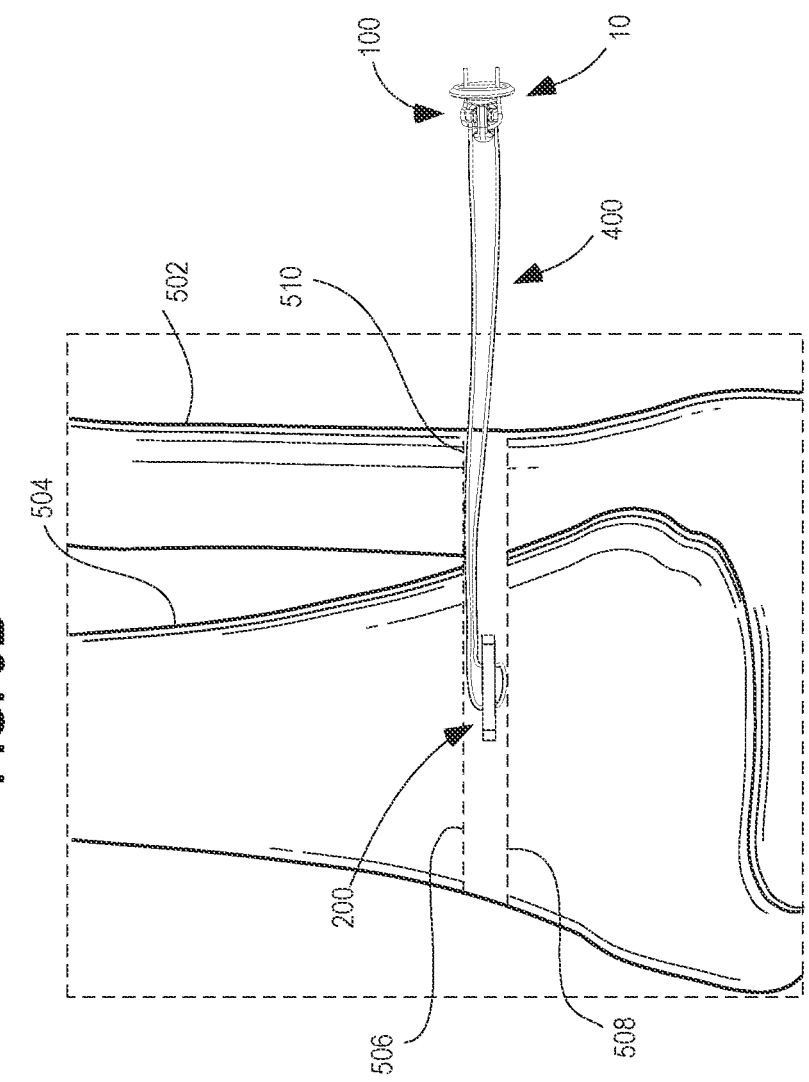

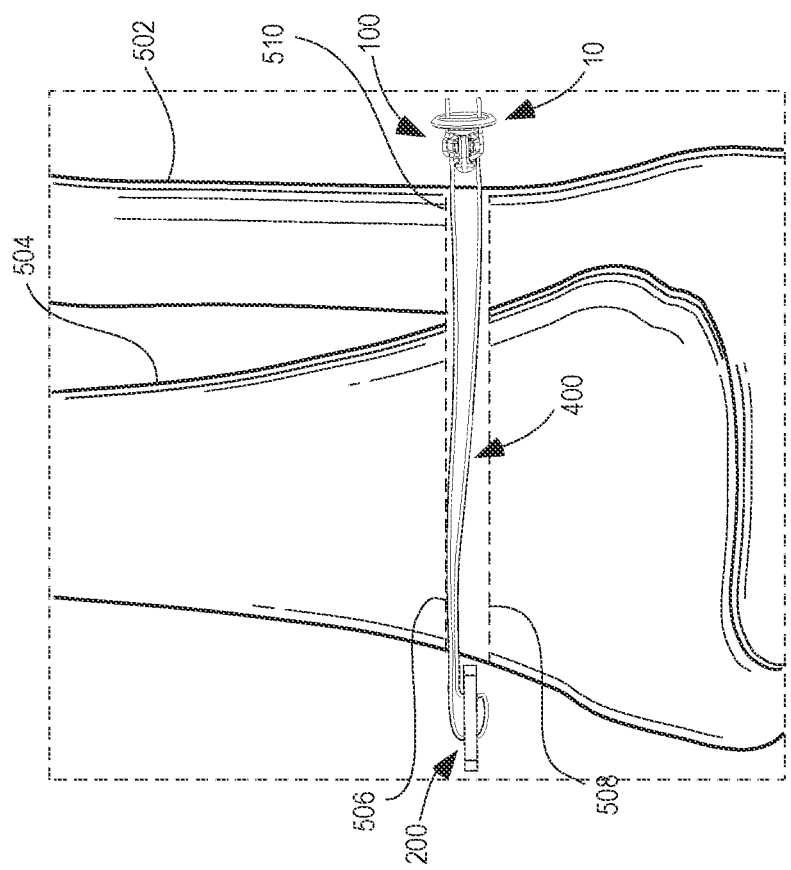

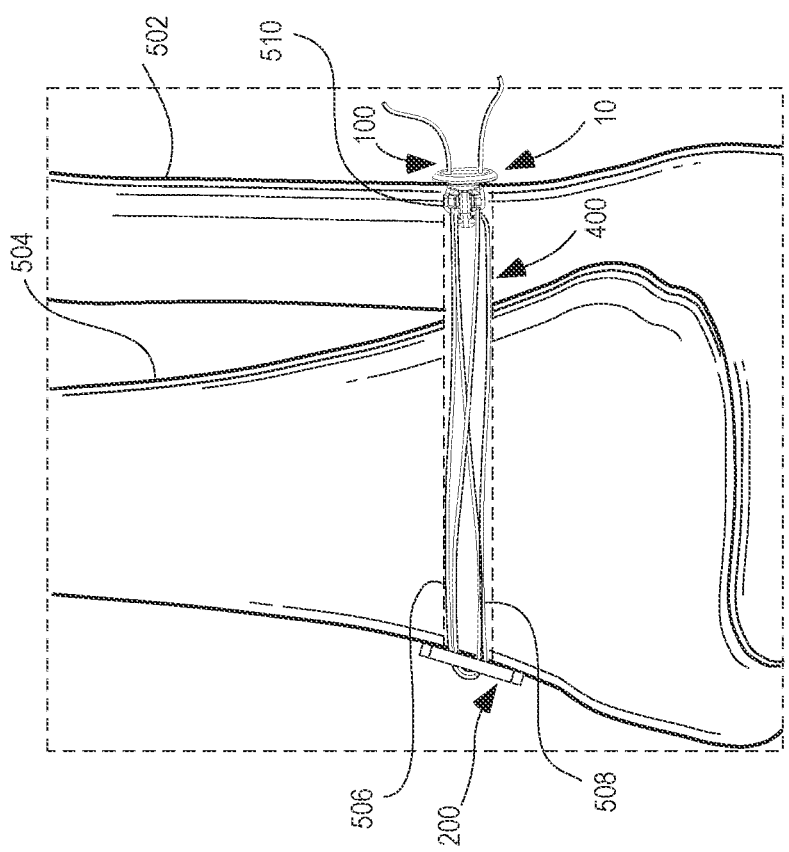

ORTHOPEDIC STABILIZATION DEVICE, KIT AND METHOD

FIELD

Orthopedic stabilization devices are described herein and, in particular button suture devices.

BACKGROUND

Numerous implants exist for repairing damaged bones and tissue. For example, fractured bones, torn joints and ligaments may be stabilized via bone plates and bone screws. Screws may not be appropriate in all applications, however. In some indications, it has been found desirable to employ various button suture devices for stabilizing certain bones or joints. Such button suture devices typically include two buttons connected via a suture, where the buttons may be positioned on opposite sides of a bone segment with suture extending therethrough in order to stabilize the bones relative to one another to promote healing. For example, button suture devices are commonly used to stabilize the tibia and fibula to repair a tear in, or damage to, the syndesmosis.

Procedures to install such button suture devices generally involve drilling a hole through the bone segment to be stabilized, advancing one of the buttons and the suture through the hole, securing the button on a far side of the bone segments, and then tightening and knotting the suture to hold the bone segments in tension. Such knotted assemblies may lose suture tension over time, and tying the knot during a surgical procedure can be burdensome.

SUMMARY

An orthopedic stabilization device is described herein, and can include a first button, a second button, a locking member and a suture. The suture extends between the first button and the second button. The suture is arranged in a pattern relative to the first button, the second button and the locking member such that tensioning of the suture can cause the locking member to move into a clamping position to restrict or fix a distance between the first button and the second button defined by one or more strands of the suture extending between the first button and the second button.

The first button can have a base portion and a depending loop. The base portion can have two first button openings extending therethrough. The loop can have an elongated loop opening therethrough. The elongated loop opening can have a major dimension and a minor dimension, the minor dimension being smaller than the major dimension. The second button can have two second button openings extending therethrough. The locking member can be slidably engaged with the loop of the first button. The locking member may have a narrow portion disposed between a pair of enlarged end portions, the narrow portion being slidingly disposed in the elongated loop opening of the first button and the enlarged end portions each having a maximum width larger than the minor dimension and smaller than the major dimension such that the enlarged end portions maintain the narrow portion in the elongated loop opening when aligned with the minor dimension and allowing the locking member to be inserted into or removed from, or disengaged with, the elongated loop opening when aligned with the major dimension. The suture extends between the first button and the second button, with a portion of the suture being frictionally retainable between the locking member and the loop to thereby tie the first button to the second button.

In one aspect, the suture extends through each of the two first button openings and each of the two second button openings. At least a first segment of the suture may extend through the elongated loop opening on an opposite side of the locking member relative to the base portion. A second segment of the suture may extend through the elongated loop opening on an adjacent side of the locking member relative to the base portion.

In another aspect, each of the enlarged end portions has a locking member opening extending therethrough and the suture extends through each of the locking member openings.

In another aspect, the locking member lacks openings.

In another aspect, the suture extends through each of the two second button openings twice. In another aspect, the suture has no more than four strands extending between the first and second buttons.

In another aspect, each of the enlarged end portions can have a locking member opening extending therethrough and the suture extends through each of the locking member openings.

In another aspect, the locking member can have a clamping position wherein the portion of the suture frictionally retainable between the locking member and the loop is clamped between the locking member and the loop on an opposite side of the locking member relative to the base portion. The suture may have free ends on an opposite side of the base portion of the first button relative to the loop, and when tension is applied on the free ends of the suture the suture moves the locking member toward the clamping position.

In one aspect, each of the enlarged end portions can have a locking member opening extending therethrough and the suture extends through each of the locking member openings, the two first button openings and the two second button openings.

A method of using the orthopedic stabilization device can include the step of applying tension on the free ends of the suture to move the locking member into the clamping position.

In another aspect, an orthopedic stabilization device is provided that has a first button having a base portion and a depending loop, the base portion having at least one first button opening extending therethrough, and the loop having an elongated loop opening therethrough. The device can also include a locking member extending through the elongated loop opening and having a clamping position and an unclamping position, the locking member being rotating within the elongated loop opening between a retained orientation, whereby the locking member can slide within the elongated loop opening but not out of the elongated loop opening, and an unretained orientation where the locking member can be inserted into or removed from the elongated loop opening. The device can also have a second button having at least one second button opening extending therethrough. The device may also include a suture extending between the first button and the second button and through the first button opening and the second button opening, with a portion of the suture being frictionally retainable between the locking member and the loop to thereby tie the first button to the second button when the locking member is in a clamping position to clamp the portion of the suture between the locking member and the loop on an opposite side of the locking member relative to the base portion.

In another aspect, an orthopedic stabilization device is provided that has a first button having a base portion and a depending loop with a loop opening, optionally elongated, extending therethrough. The base portion has two first button openings extending therethrough. A locking member is slidably engaged with the loop of the first button, the locking member having two locking member openings extending therethrough. A second button is also provided, having two second button openings extending therethrough. A suture extends between the first button and the second button, with a portion of the suture being frictionally retainable between the locking member and the loop to thereby tie the first button to the second button, wherein the suture extends through each of the two first button openings, each of the two second button openings, and each of the two locking member openings. Having the suture extend through locking member openings can help to maintain the locking member at least partially within the loop.

In another aspect, a first segment and a second segment of the suture extends through the elongated loop opening on an opposite side of the locking member relative to the base portion. A second segment of the suture may extend through the elongated loop opening on an adjacent side of the locking member relative to the base portion. The locking member may have a clamping position wherein the portion of the suture frictionally retainable between the locking member and the loop is clamped between the locking member and the loop on an opposite side of the locking member relative to the base portion.

The suture may have free ends on an opposite side of the base portion of the first button relative to the loop. The suture can be arranged in a pattern such that when tension applied on the free ends of the suture the locking member moves toward a clamping position. A method of using the orthopedic stabilization device of may include applying tension on the free ends of the suture to move the locking member into the clamping position to clamp the first segment and the second segment of the suture between the locking member and the loop.

BRIEF DESCRIPTION OF THE DRAWINGS

FIG. 3A is a perspective view of the second button of FIG. 1;

FIG. 9A is a side elevational view of a surgical site showing a bore through the fibula and tibia of a patient's leg and the stabilization device of FIG. 1 positioned for placement within the bore;

FIG. 9B is a side elevational view of the surgical site of FIG. 9A showing the second button of the orthopedic stabilization device of FIG. 1 being advanced through the bone hole;

FIG. 9C is a side elevational view of the surgical site of FIG. 9A showing the second button seated and abutting the far cortex of the tibia, with first and second ends of the suture extending from openings of the first button and the suture not under tension;

FIG. 9D is a side elevational view of the surgical site of FIG. 9A showing the suture under tension such that the first button is seated against the near cortex of the fibula and wherein the first button is tied to the second button by the suture thereby tying the fibula to the tibia;

DETAILED DESCRIPTION

Figure 1:
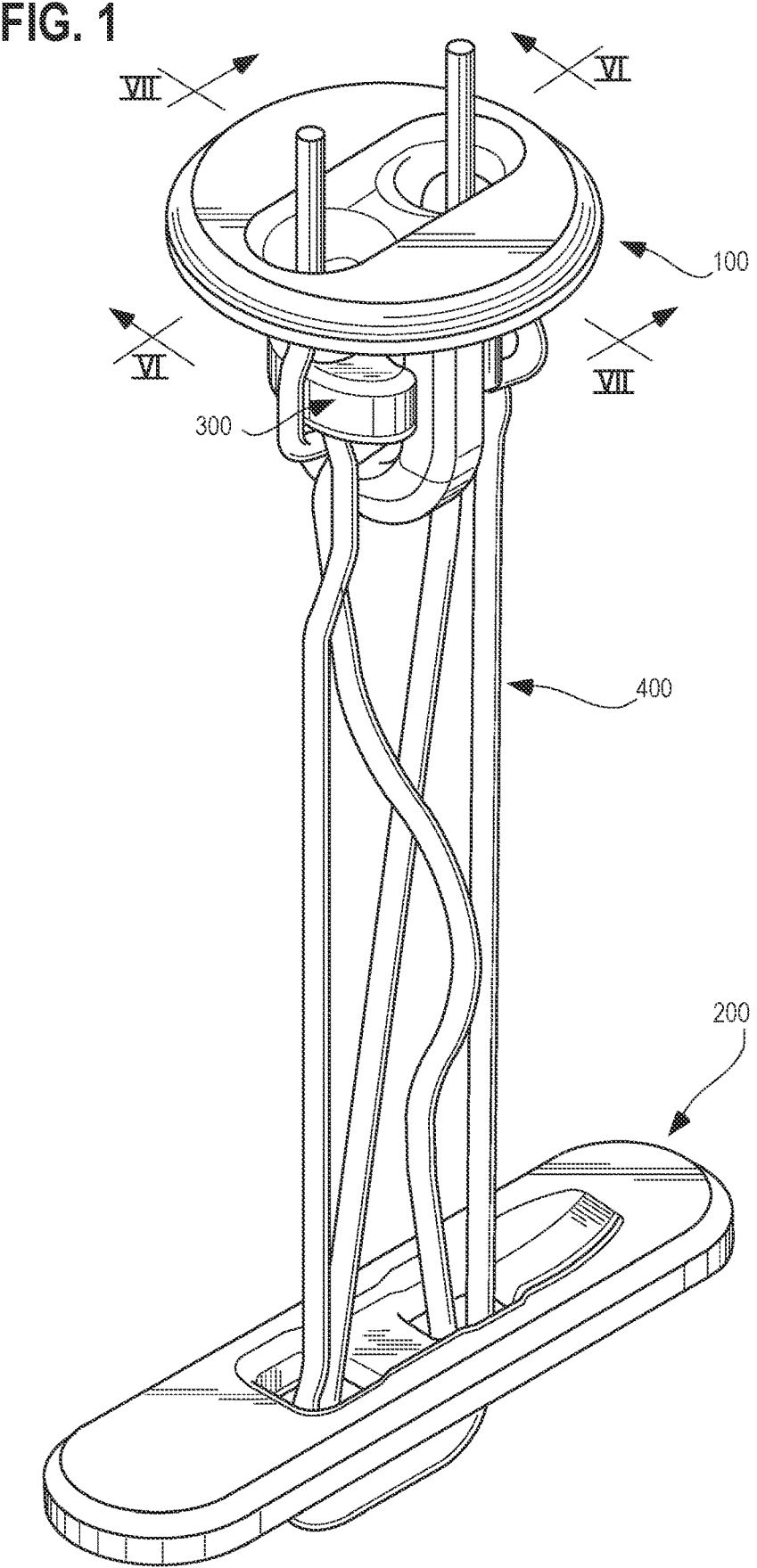
FIG. 1 is a perspective view of a first embodiment of an orthopedic stabilization device having a first button with a base and a depending loop, a locking member extending through an elongated opening of the loop, a second button and a suture extending between the first and second buttons.
Figure 2A:
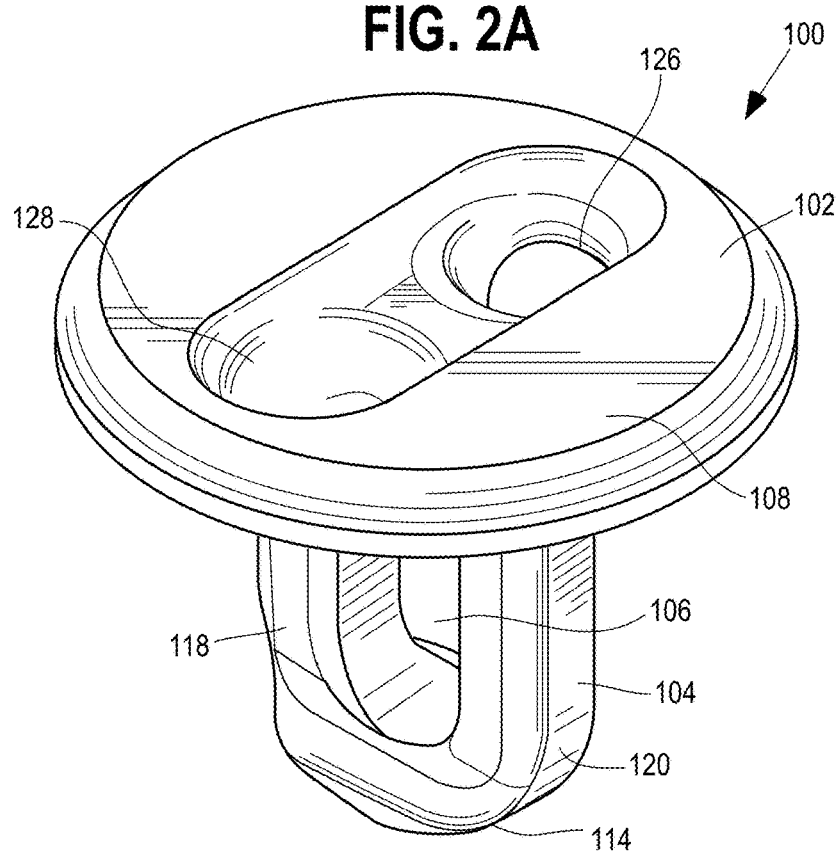
FIG. 2A is a perspective view of the first button of FIG. 1.
Figure 2B:
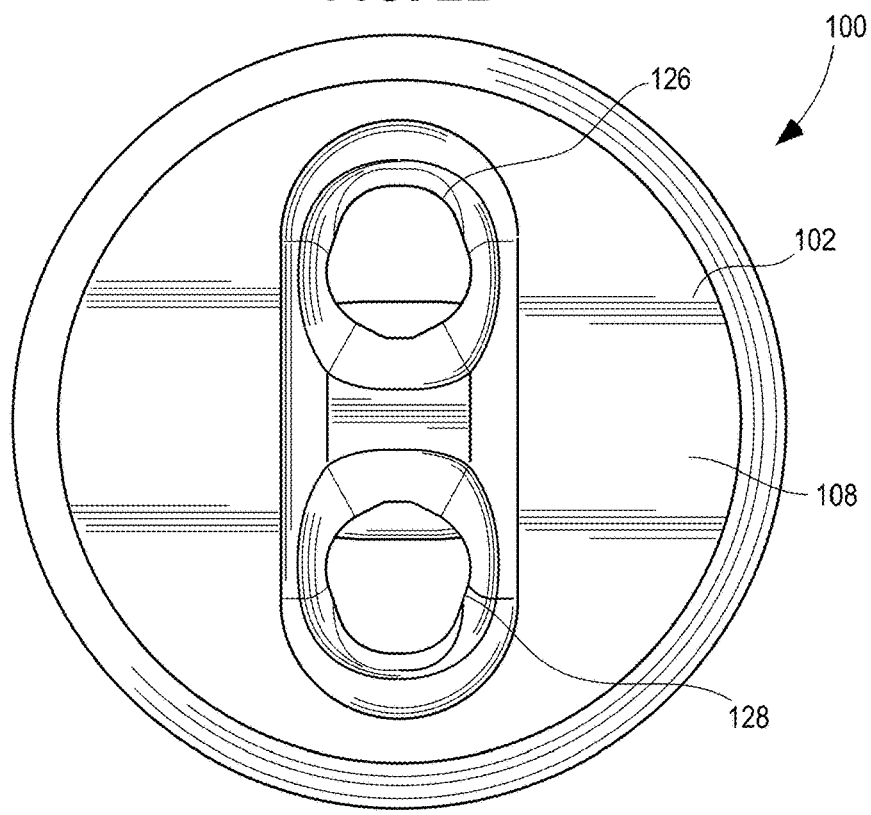
FIG. 2B is a top plan view of the first button of FIG. 1, showing a pair of first button openings.
Figure 2C:
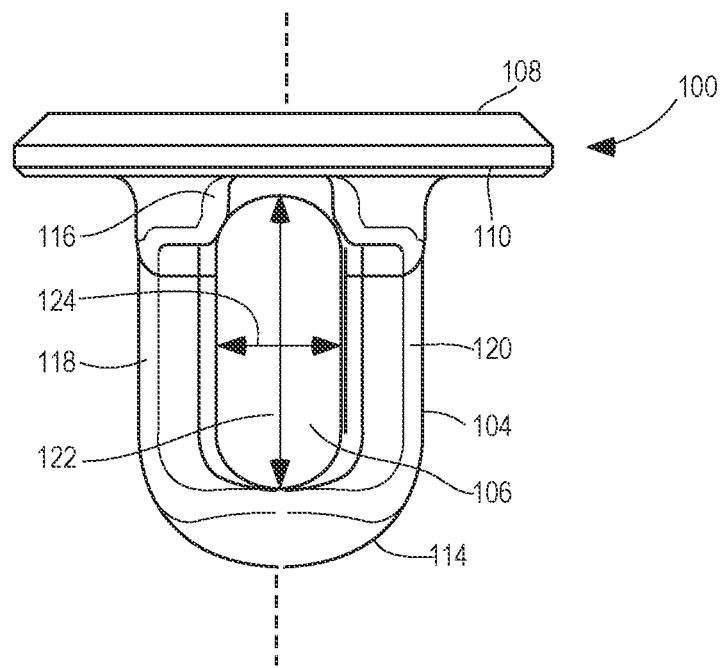
FIG. 2C is a right-side elevation view of the first button of FIG. 1.
Figure 2D:
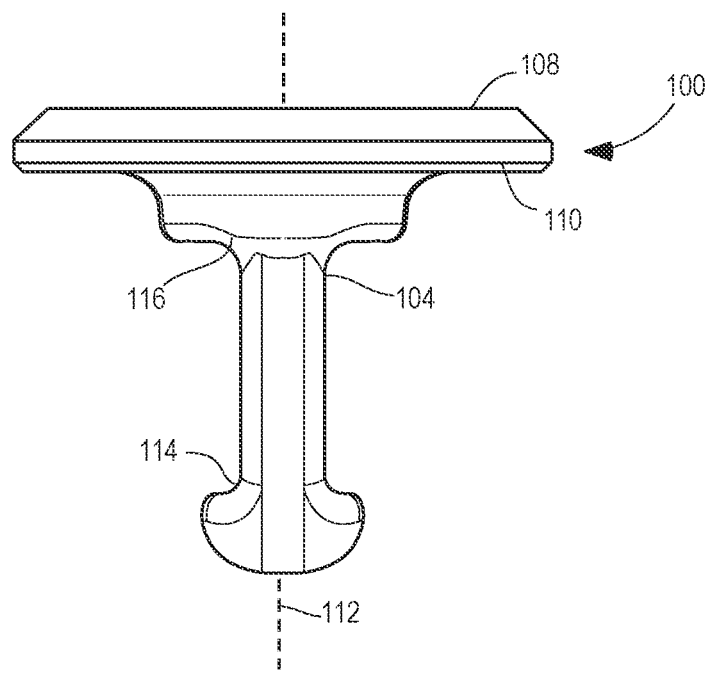
FIG. 2D is a front side elevation view of the first button of FIG. 1.

A non-limiting, exemplary embodiment of an orthopedic stabilization device 10 is provided having a first button 100, a second button 200 and a suture 400 extending therebetween, as shown in the first exemplary embodiment of FIGS. 1-8. The first button 100 has a base portion 102 and a depending loop 104 having an elongated loop opening 106 therethrough. A locking member 300 extends through the elongated loop opening 106 and, advantageously, is retained with the loop 104 when in a retained orientation and insertable, during assembly, or removable, after assembly, when in an unretained orientation, as will be described in greater detail herein. One or more portions of the suture 400 are frictionally retainable between the locking member 300 and the loop 104 of the first button 100 to thereby tie the first button 100 to the second button 200 when the locking member 300 is in a clamping position, actuated upon tensioning of the suture 400, as will be described further herein.

Turning to the structural details of the device 10, the base portion 102 of the first button is disc-shaped with a top side 108 and a bottom side 110, as shown in FIGS. 2A-2D. The loop 106 depends from the bottom side 110 in a direction along a central axis 112 passing through a center of the base portion 102. The depending loop 104 has a curved, distal end 114 and a proximate end 116 connected to the bottom side 110 of the base portion 102. Both the distal end 114 and the proximate end 116 of the loop 104 are outwardly flared compared to a pair of spaced sides 118, 120. Having the distal end 114 and the proximate end 116 of the loop 104 outwardly flared can help facilitate movement of the suture 400 thereagainst and reduce breaking of the suture 400. The elongated loop opening 106 is generally oval or race-track shaped, although other shapes can also be suitable. The elongated loop opening 106 has a major dimension 122—coinciding with the central axis 112—and a minor dimension 124—orthogonal to the central axis 112 and at a midpoint of the major dimension 122. The major dimension 122 is larger than the minor dimension 124, for purposes of which will be described further herein. The base 102 of the first button 100 has a pair of first button openings 126, 128 extending therethrough.

Figure 3B:
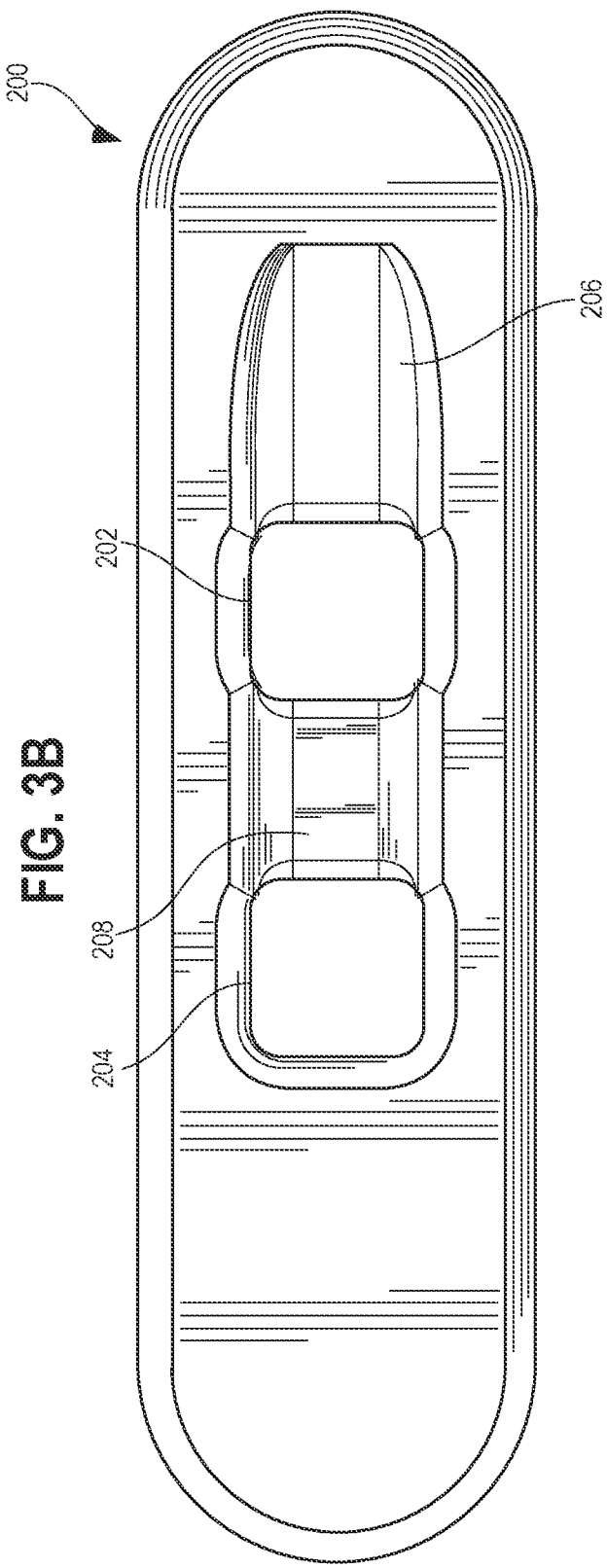
FIG. 3B is a top plan view of the second button of FIG. 1, showing a pair of second button openings.

The second button 200 is shown as a generally flat plate, as shown in FIGS. 3A and 3B, although other shapes may be suitable. The second button 200 has two second button openings 202, 204 extending therethrough for receiving the suture 400, as will be explained further herein. A scalloped region 206 is disposed on both sides of the second button 200 adjacent one of the second button openings 204. A bridge 208 between the two second button openings 202, 204 is thinned compared to the thickness of the second button. The purpose of the scalloped regions 206 and the thinned bridge 208 is to facilitate the suture 400 laying thereagainst during insertion to reduce the profile of the second button 200 with the suture 400 threaded through the second button openings 202, 204. Reducing the profile of the second button 200 with the suture 400 threaded through can help facilitate insertion of the second button 200 through a bore in a bone, as discussed in further detail below and with reference to the exemplary embodiment depicted in FIGS. 9A-9D.

Figure 4A:
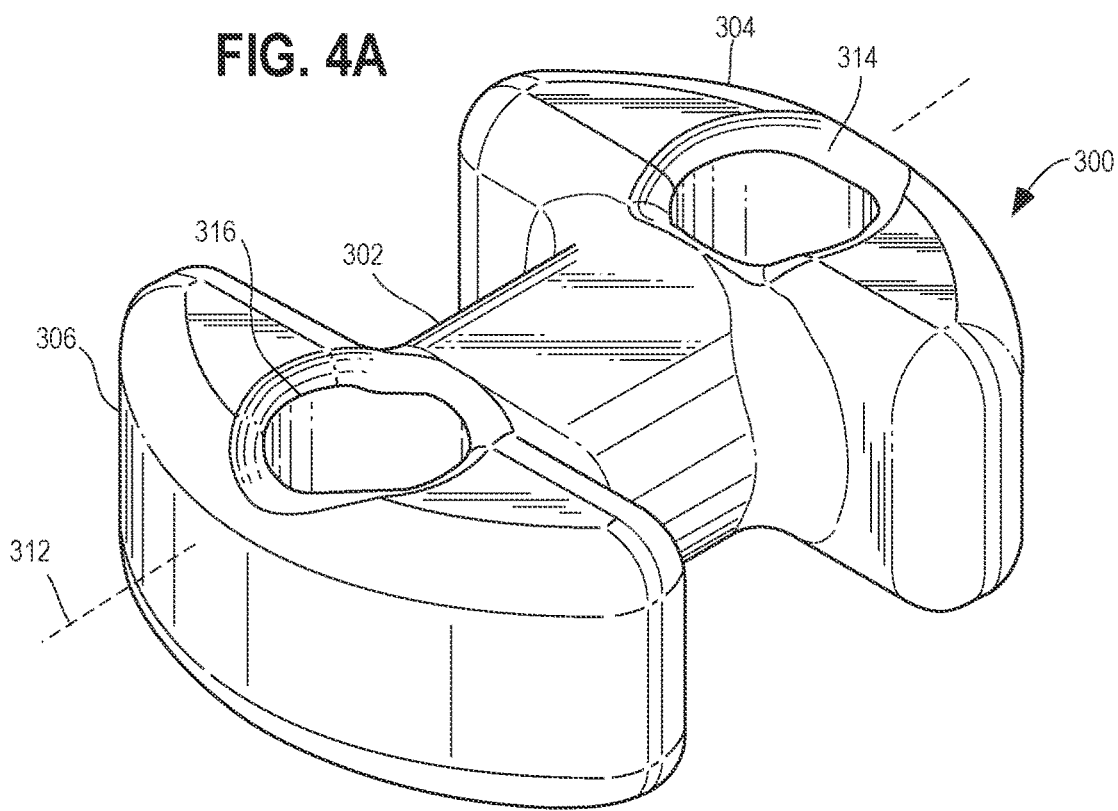
FIG. 4A is a perspective view of the locking member of FIG. 1.
Figure 4B:
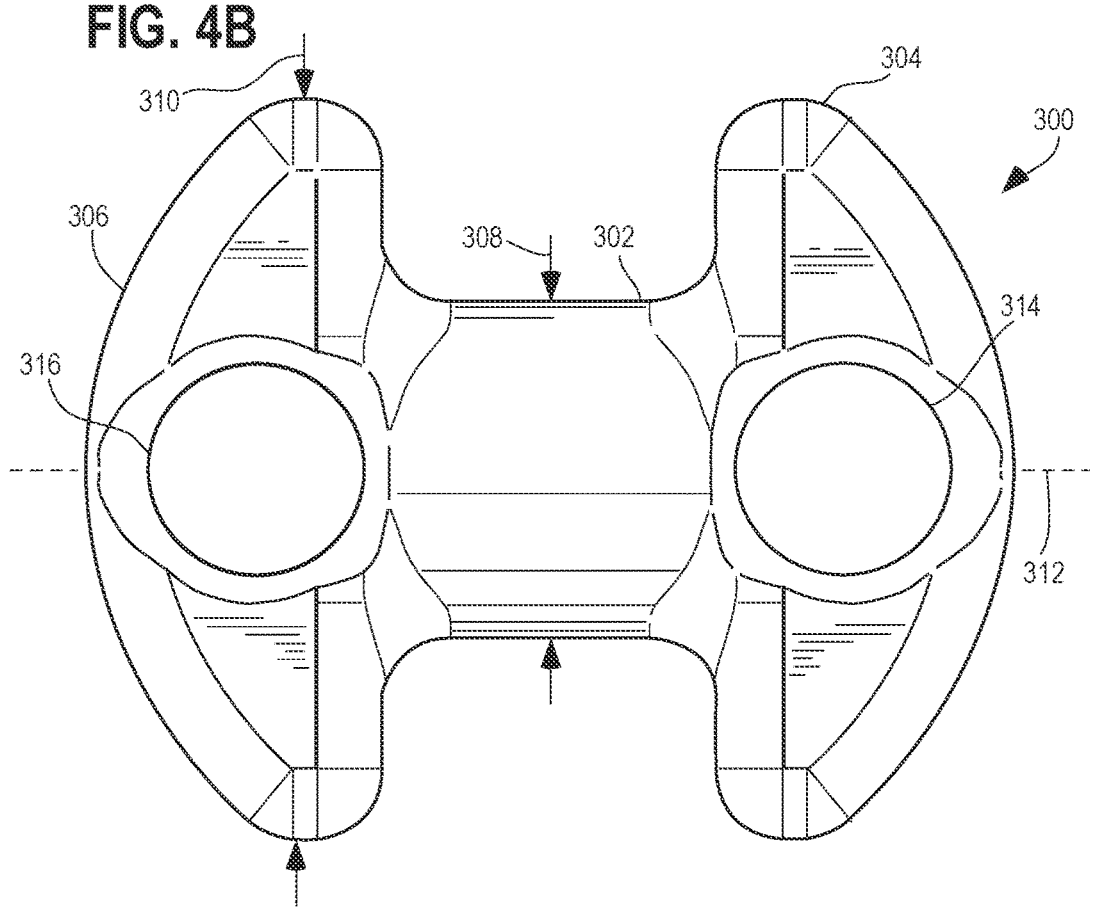
FIG. 4B is a top plan view of the locking member of FIG. 1, showing a pair of locking member openings.
Figure 5A:
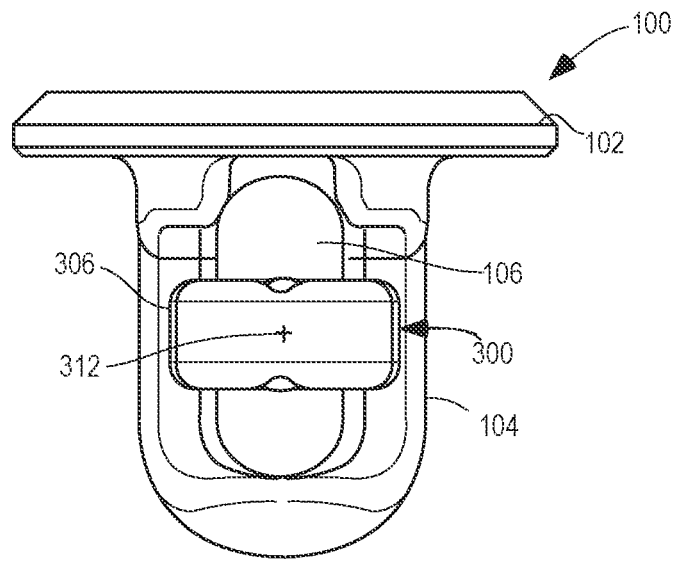
FIG. 5A is a right-side elevation view of the first button and locking member of FIG. 1, with the locking member in a retained orientation whereby removal from the loop of the first button is restricted.
Figure 5B:
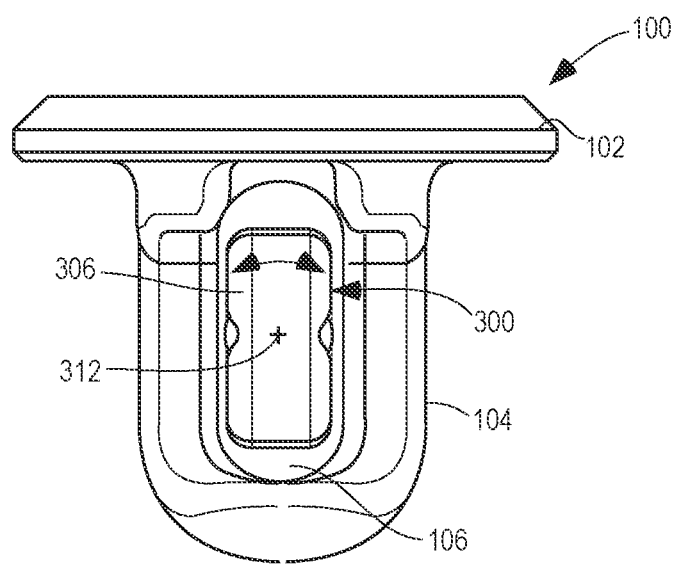
FIG. 5B is a right-side elevation view of the first button and locking member of FIG. 1, with the locking member being rotated with the elongated loop opening of the first button relative to the depiction in FIG. 5A to an unretained orientation, with the locking member being able to be removed from the loop of the first button.

The locking member 300 is generally a flattened dumbbell shaped, with a narrow portion 302 disposed between a pair of enlarged end portions 304, 306, as shown in FIGS. 4A and 4B. The narrow portion 302 is dimensioned to be slidingly disposed in the elongated loop opening 106 of the first button 100 when assembled. For example, the narrow portion 302 can have a narrow dimension 308 that is less than the minor dimension 124 of the elongated loop opening 106 of the loop 104 of the first button 100. The enlarged end portions 304, 306 each have a maximum locking member dimension 310 larger than the minor dimension 124 but yet smaller than the major dimension 122. When in a first orientation, shown in FIGS. 1 and 5A, the enlarged end portions 304, 306 maintain the narrow portion 302 in the elongated loop opening 106 when aligned with the minor dimension 124. However, when rotated about a locking member axis 312 until aligned with the major dimension 122, as shown in FIG. 5B, the enlarged end portions 304, 306 are able to pass through the elongated loop opening 106. These dimensions 122, 124, 308, 310 allow the locking member 300 to be readily assembled by inserting the locking member 300 through the elongated loop opening 106, but then retained once the locking member 300 is rotated about the locking member axis 312. Optionally, each of the enlarged end portions 304, 306 have a locking member opening 314, 316 for receiving the suture 400, as will be explained in further detail.

The suture 400 extends between the first button 100 and the second button 200, with one or more portions of the suture 400 being frictionally retainable between the locking member 300 and the loop 104 of the first button 100 to thereby tie the first button 100 to the second button 200 when tension is applied to the suture 400. This allows a distance between the first button 100 and the second button 200 to be restricted from increasing. In use, restricting or fixing the distance between the first button 100 and the second button 200 allows for the device to be used in holding two bones together, as described further below.

Figure 6:
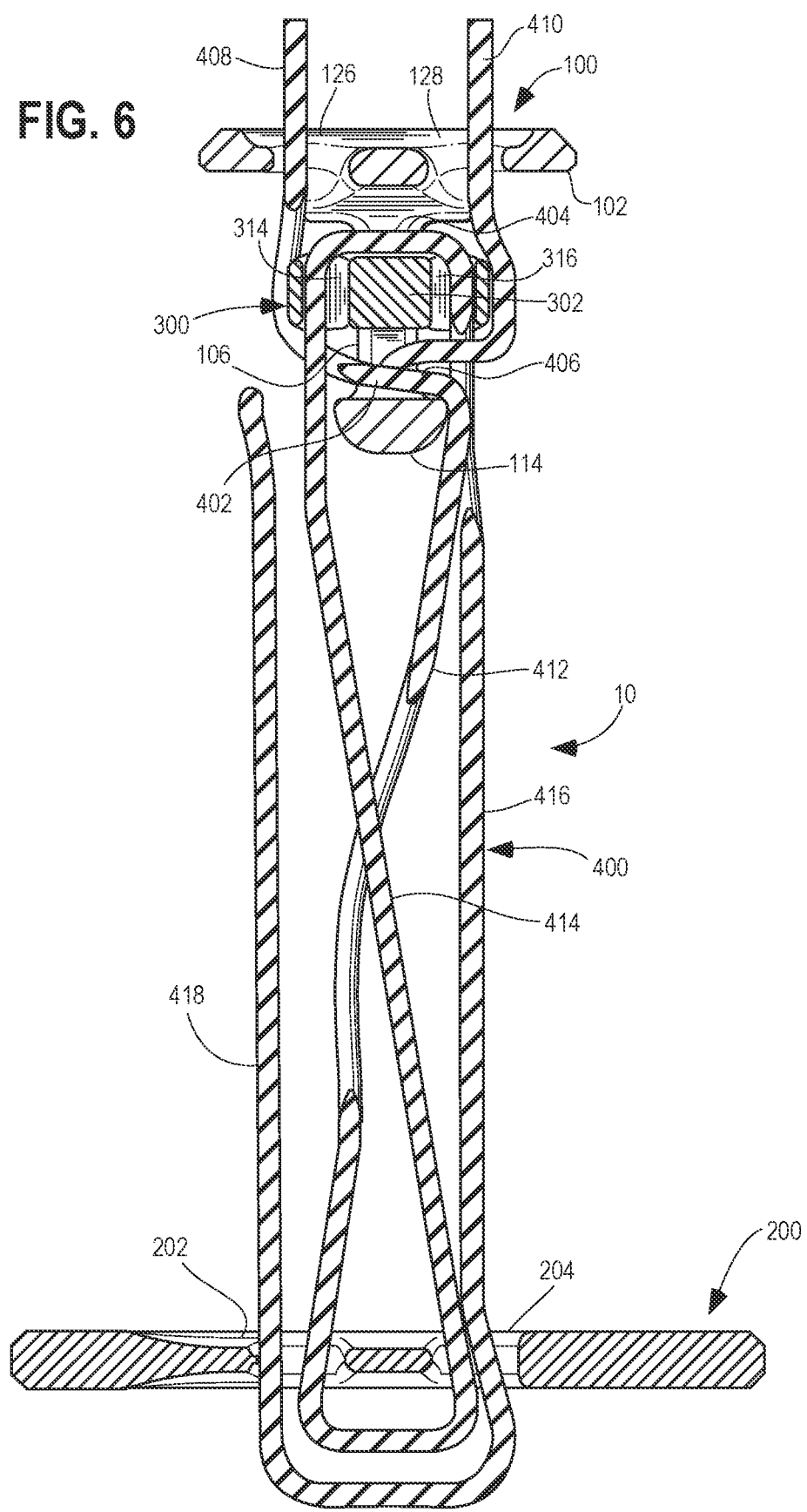
FIG. 6 is a cross-sectional view of the orthopedic stabilization device of FIG. 1 taken along line VI-VI thereof.
Figure 7:
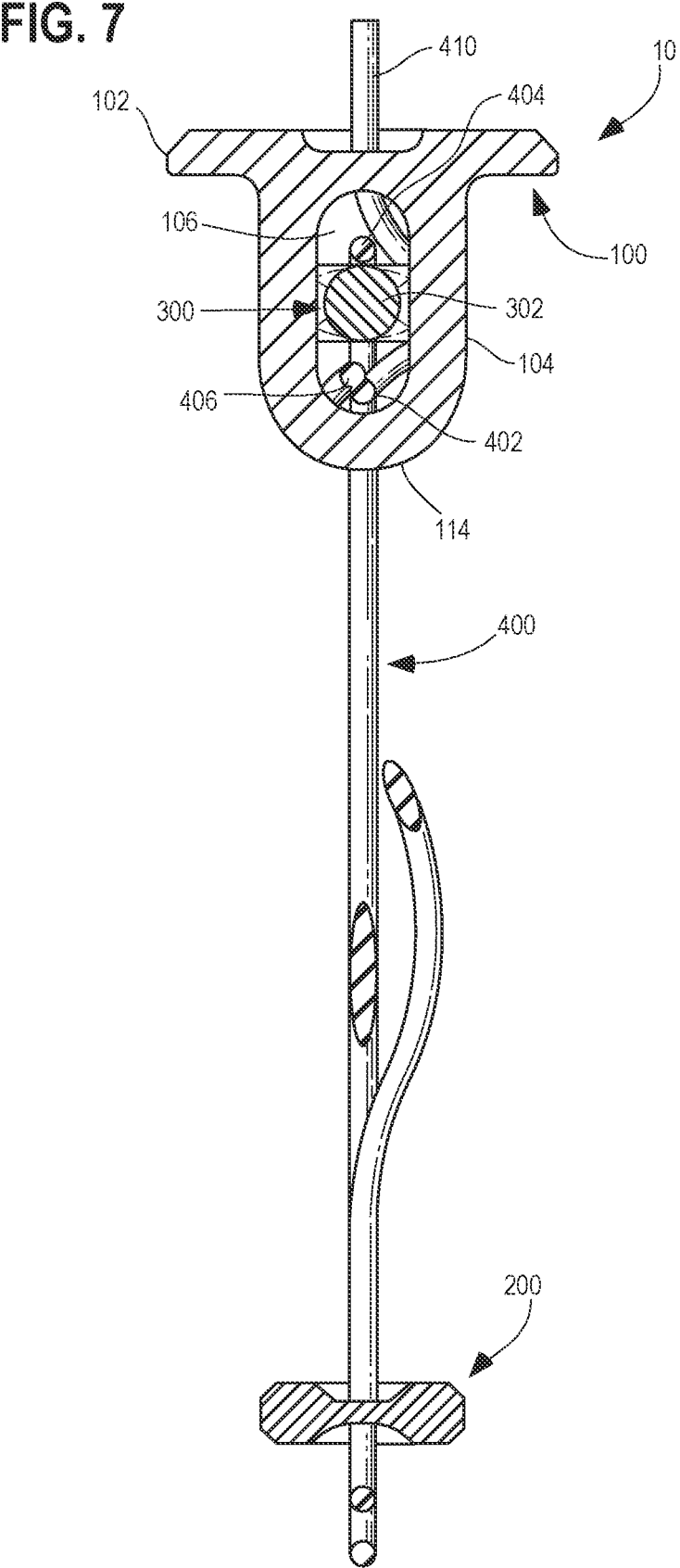
FIG. 7 is a cross-sectional view of the orthopedic stabilization device of FIG. 1 taken along line VII-VII thereof.

The suture 400 can be considered to have multiple segments and strands, as shown in FIGS. 6 and 7. Although shown as being continuous, the suture 400 can be formed of multiple pieces joined together. The suture 400 has a first segment 402 that extends through the elongated loop opening 106 on an opposite side of the locking member 300 relative to the base portion 102 of the first button 100. The suture 400 also has a second segment 404 that extends through the elongated loop opening 106 on an adjacent side of the locking member 300 relative to the base portion 102 of the first button 100. The suture 400 also has a third segment 406 extends that through the elongated loop opening 106 on an opposite side of the locking member 300 relative to the base portion 102 of the first button 100. The suture 400 also has a pair of free ends 408, 410.

The suture 400 is arranged in a pattern such that tensioning the free ends 408, 410 causes the second segment 404 of the suture 400 to pull the locking member 300 toward the curved, distal end 114 of the loop 104 and away from the base 102 of the first button 100 to move the locking member 300 toward the clamping position and clamp the first and third segments 402, 406 of the suture 400 between the narrow portion 302 of the locking member 300 and an interior side of the distal end 114 of the loop 104 within the enlarged loop opening 106. With the first and third segments 402, 406 of the suture 400 so clamped, the suture 400 is restricted or prevented from movement that would allow the first button 100 and the second button 200 to move further apart. In other words, the distance between the first button 100 and second button 200 is restricted or fixed against increasing.

The suture 400 can be arranged in a pattern, as shown in FIGS. 1 and 6-8A, that extends through each of the two first button openings 126, 128, each of the two second button openings 202, 204 and each of the two locking member openings 314, 316. More specifically, and starting with a first 408 of the free ends 408, 410 of the suture 400, the suture 400 extends through a first 126 of the first button openings 126, 128, under the locking member 300 and through the elongated loop opening 106—defining the first segment 402 of the suture 400—and then through a first 202 of the second button openings 202, 204 to a side of the second button 200 opposite the first button 100. The suture 400 then extends through a second 204 of the second button openings 202, 204 and through a first 314 of the locking member openings 314, 316 to a side of the locking member 300 facing the base portion 102 of the first button 100, through the elongated loop opening 106 of the first button 100 and then through a second 316 of the locking member openings 314, 316, thereby defining the second segment 404 of the suture 400 extending between the locking member openings 314, 316 on a side of the locking member 300 facing the base portion 102 of the first button 100. The suture 400 then extends through the second 204 of the second button openings 202, 204 to the opposite side of the second button 200, then through the first 202 of the second button openings 202, 204 and through the elongated loop opening 106 between the locking member 300 and the distal end 114 of the loop 104, and then through a second 128 of the first button openings 126, 128. This results in a pattern where the suture 400 has four strands 412, 414, 416, 418 extending between the first button 100 and the second button 200. Preferably, though not necessarily, there are only four strands 412, 414, 416, 418 or, alternatively, no more than four strands. As shown in FIGS. 1 and 6-8A, there are two lateral strands 416, 418 and a pair of intermediate crossing strands 412, 414.

Although described as free ends, the ends 408, 410 of the suture 400 can be tied together and function the same, e.g., tensioning causes the locking member 300 to move toward the clamping position. Alternatively, a portion of the suture could be disposed on an opposite side of the base portion 102 relative to the loop 104 and tensioned to move the locking member 300 toward the clamping position. In yet another alternative, one of the portions of the suture 400, on an opposite side of the second button 200 from the first button 100, could be tensioned to move the locking member 300 toward the clamping position.

An alternative pattern for a suture 1400, depicted in FIGS. 8B and 13-15, can be used instead of the pattern for the suture 400 depicted in FIGS. 1 and 6-8A. The alternative pattern for the suture 1400 is described in further detail below with respect to an alternative, second embodiment of the orthopedic stabilization device 1010, depicted in FIGS. 13-16B.

The first button 100, second button 200 and locking member 300 may be made of titanium, a stainless-steel alloy, a polyether ether ketone (PEEK) material, or a poly-L-lactic acid (PLLA) material, or an alternative bioresorbable material. The first button 100, second button 200 and locking member 300 may be made of the same material, different materials, or combinations thereof.

The suture 400 may be manufactured out of a variety of filaments or fibers including, by way of example, polymer filaments, metallic filaments, and organic filaments. Alternatively, the suture 400 may be a suture braid having braided filaments such as high strength #5 braided suture. In other forms, the suture 400 may be formed of ultrahigh molecular weight polyethylene braided with strands of polyester, collagen, silk, nylon, among other suture materials.

Additionally, the suture 400 may be formed of different lengths depending on the surgical application. The suture 400 should be of a sufficient length that it may looped around the first button 100 and the second button 200 and around the locking member 300 to provide an amount of slack to allow the device 10 to be installed in its intended application, and thereafter tensioned, in a variety of applications.

With reference to FIGS. 9A-9D, an example method of stabilizing a bone using the orthopedic stabilization device 10 is depicted. More specifically, FIGS. 9A-9D depict a method of stabilizing the syndesmosis and show a tibia 504 and a fibula 502 of a patient with the syndesmosis positioned therebetween. Referring now to FIG. 9A, a tibia 504 and a fibula 502 are shown after being surgically exposed and having a bore 506 drilled therethrough (i.e., a fibular tunnel 510 and a tibia tunnel 508) for receiving the orthopedic stabilization device. To create the bore 506, an incision may be made on the lateral side of the patient's leg to expose a portion of the fibula 502. A surgical drill bit 602 may then be used to bore a hole through the fibula 502 and tibia 504 to facilitate insertion and installation of the orthopedic stabilization device 10. In other forms, a guide wire (e.g., guide wire 604 shown in FIG. 12) may be inserted through the bones prior to drilling such that a cannulated drill bit may be received on and advanced along the guide wire to drill the bore 506 through the bones. The bore 506 is sized to accommodate insertion of the second button 200 therethrough when the second button 200 is positioned in a flat configuration (shown in FIG. 9B).

Figure 12:
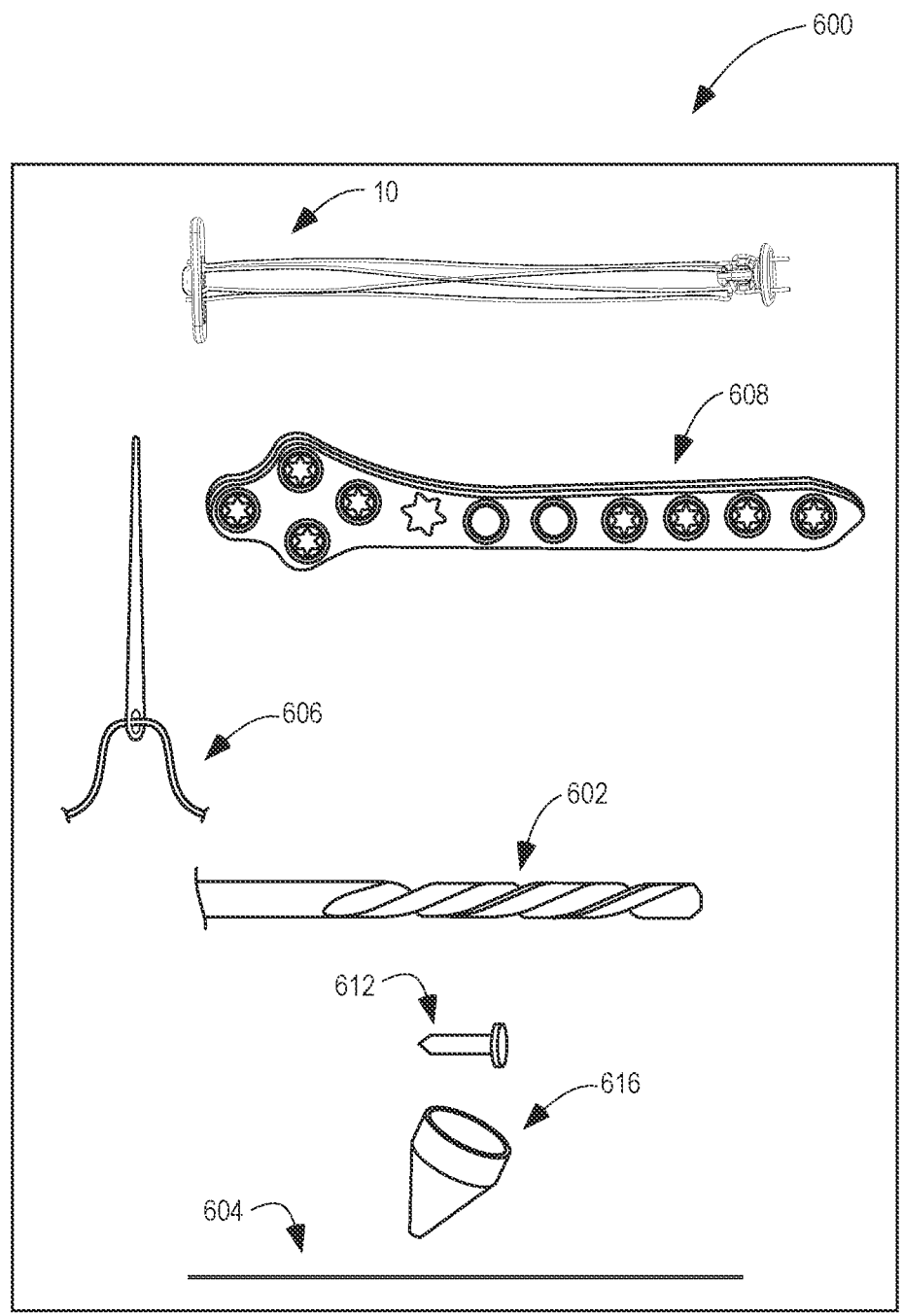
FIG. 12 shows an exemplary kit including the orthopedic stabilization device of FIG. 1, a drill bit, a drill guide, and a passing device, among other optional components.

FIG. 9B shows the second button 200 of the orthopedic stabilization device 10 being advanced through the bore 506 drilled through the bone segments shown in FIG. 9A. The second button 200 may be advanced through the bone bore 506 in the flat configuration to exit the far cortex of the tibia 504 as shown in FIG. 9B in a variety of ways. For example, the second button 200 may be pulled through the bone bore 506 from the lateral side to the medial side using a pin or needle-like passing device 606 (such as shown in FIG. 12) such that the second button 200 exits the bone bore 506 proximate the medial portion of the tibia 504. For example, the passing device 606 may include a portion of suture or string coupled to the second button 200 (e.g., through the second button openings 202, 204) such that the needle-like passing device 606 may be advanced through the bore 506, and through the patient's skin on the medial portion of the tibia 504. Thereafter, the passing device 606 may be used to pull the second button 200 through the bore 506 and manipulate positioning thereof against the medial portion of the tibia 504 via the suture or string coupled to the second button 200. In such forms, it may be desirable or necessary to make a small incision in the medial size of the tibia 504 to adjust or manipulate the second button 200 once it exits the far cortex thereof.

Referring to FIG. 9C, the second button 200 is shown having been advanced through the bone bore 106 and flipped from the flat configuration, so a distal surface of the second button 200 is seated against and abutting the medial cortex of the tibia 504. At this step, the suture 400 and the first and second buttons 100, 200 are not yet held in tension, and the first button 100 is not yet in contact with the near cortex of the fibula 502. Once the second button 200 is secured against the medial cortex, the device 10 may be tensioned to tie the first button 100 to the second button 200 and thereby tie bone segments, the suture 400 in this position shown cinched between the locking member 300 and the loop 104 of the first button 100.

In FIG. 9D, tension has been applied to the orthopedic stabilization device 10. As described above, the second segment 404 of the suture 400 will pull the locking member 300 away from the base portion 102 of the first button 100 and toward the inner side of the distal end 114 of the loop 104 of the first button 100 such that the first segment 402 and the third segment 406 of the suture 400 will be clamped and thereby frictionally retained between the locking member 300 and the loop 104. So configured, the orthopedic stabilization device 10 is inhibited from loosening once in the tensioned state due to the frictional retainment of the suture 400 between the locking member 300 and the loop 104 of the first button 100. Additionally, the free ends 408, 410 of the suture 400, if present, are not required to be knotted once tensioned. In alternative embodiments, free ends of the suture may extend from the second button 200 such that the device 10 may be tensioned on the medial side of the bone segment (e.g., the tibia 504 in FIGS. 9A-9D) upon installation therein. In either case, it is contemplated that the buttons 100, 200, locking member 300 and suture 400 will be assembled by the manufacturer and not by the surgeon or hospital staff. It is contemplated in some embodiments that the buttons 100, 200, locking member 300 and suture 400 may be provided unassembled, for surgeons that have a preference as to the configuration of the device 10.

Figure 10:
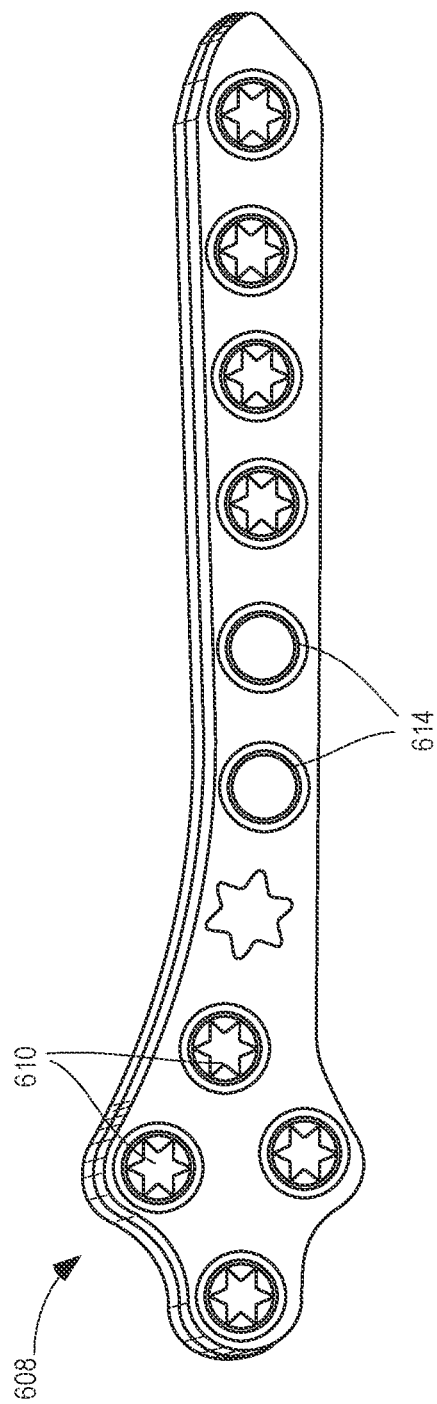
FIG. 10 is a perspective view of a bone plate having an opening sized to receive the first button of the orthopedic stabilization device of FIG. 1.

In other forms, the orthopedic stabilization device 10 may be used in connection with a bone plate (e.g., the bone plate 608 shown in FIGS. 10 and 12) such that the bone plate 608 is positioned between the first button 100 and the surface of the bone 504. For example, such a bone plate 608 may be used to repair a fracture, ligament, or joint. Referring to FIG. 10, an exemplary lateral fibula bone plate 608 is shown including a plurality of openings 610 sized to receive bone screws 612 therethrough to secure the bone plate 608 to a portion of bone. The orthopedic stabilization device 10 may be used in connection with bone plates of a variety of shapes, sizes, and having differing numbers of openings. In some embodiments, openings 614 may be specifically sized to seat the first button 100 thereon. For example, the openings 614 shown in FIG. 10 are configured to at least partially receive the first button 100 such that the first button 100 may be seated therein once the device 10 has been tensioned. In some forms, the bone plate 608 may include two or more openings 614 such that multiple orthopedic stabilization devices 10 may be installed to improve the compressive force or otherwise promote tissue healing or repair.

Figure 11:
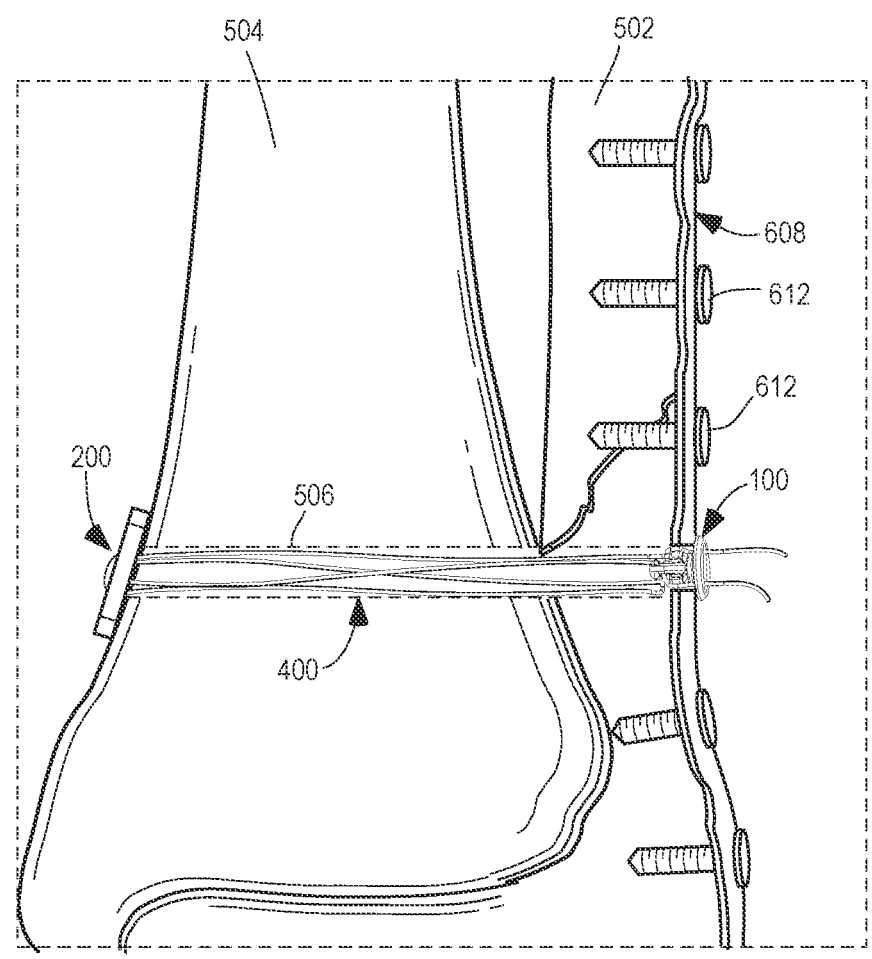
FIG. 11 is a side elevational of a surgical site where the bone plate of FIG. 10 and the orthopedic stabilization device of FIG. 1 are installed in a bone segment of a patient.

As shown in FIG. 11, the bone plate 608 of FIG. 10 has been positioned proximate the fibula 502 and screwed into place via bone screws 612 to secure the plate 608 thereto, preferably after a fracture shown in the fibula 502 has been reduced. Thereafter, the bore 506 is drilled through the fibula 502 and tibia 504 as hereinbefore discussed, and the orthopedic stabilization device 10 may thereafter be installed generally as described above.

As shown in FIG. 12, a kit 600 may be provided including a number of components, such as the orthopedic stabilization device 10 and one or more of the other components shown, including a drill bit 602, a drill guide 616, a guide wire 604, a passing device 606, a bone plate 608, a bone screw 612 (or a plurality thereof), and any other suitable component. It is contemplated that the kit 600 will include at least the orthopedic stabilization device 10, drill bit 602, and drill guide 616, and optionally the guide wire 604. The drill bit 602 may be provided in a variety of sizes depending on a desired size of the bore 506. Additionally, the drill guide 616 may be provided to inhibit irritation of surrounding tissue while, for example, a bore 506 is being drilled into the one or more bone segments by the drill bit 602. The kit 600 may be provided in the form of a sealed package containing the above-enumerated components or combinations thereof. Variants of the kits including different components and different embodiments of the orthopedic stabilization device 10 provided herein could be provided for different procedural indications. For example, a kit may be provided including an embodiment of the orthopedic stabilization device omitting the second button such that the suture may be coupled to a portion of tissue or another structure and tensioned between the tissue or structure and the first button 100.

As described above, the passing device 606 may be coupled to the orthopedic stabilization device 10 to shuttle the second button 200 and suture 400 through the bore 506 drilled via the drill bit 602 such that the second button 200 may be positioned proximate the far cortex of the bone 504. In some forms, the passing device 606 may be needle-like and coupled to the second button 200 via a portion of string or suture for pulling the second button 200 and suture 400 looped therearound. In other forms, the passing device 606 may include an insertion tool such that the tool may push or carry the second button 200 through the bore 506 and dispose the second button 200 on the far cortex of the bone 504, such that an incision near the far cortex may not be required.

A non-limiting, exemplary embodiment of an orthopedic stabilization device 1010 is provided having a first button 1100, a second button 1200 and a suture 1400 extending therebetween, as shown in the second exemplary embodiment of FIGS. 13-16B The first button 1010 is the same as that of the first embodiment of FIGS. 1-8, having a base portion 1102 and a depending loop 1104 having an elongated loop opening 1106 therethrough. A locking member 1300 extends through the elongated loop opening 1106. One or more portions of the suture 1400 are frictionally retainable between the locking member 1300 and the loop 1104 of the first button 1100 to thereby tie the first button 1100 to the second button 1200 when the locking member 1300 is in a clamping position, actuated upon tensioning of the suture 1400, as will be described further herein. Details of structure, construction, operation and methods of stabilizing a bone for the second embodiment of the orthopedic stabilization device 1010 are the same as that of the first embodiment of the orthopedic stabilization device 10 unless otherwise described or depicted. For example, the materials of the second embodiment of the orthopedic stabilization device 1010 can be the same as those discussed above with respect to the first embodiment of the orthopedic stabilization device 10. Also by way of example, the orthopedic stabilization device 1010 of the second embodiment and/or the locking member 2300 described herein can be substituted for use in the methods and kits depicted in FIGS. 9A-12 and/or discussed above.

The orthopedic stabilization device 1010 of the second embodiment differs from the orthopedic stabilization device 10 of the first embodiment in that a different locking member 1300 is used. The locking member 1300 is cylindrical in shape, as shown in detail in FIGS. 16A and 16B, and has a pair of through openings 1314 and 1316. Unlike the locking member 300 of the first embodiment of the orthopedic stabilization device 10, the locking member 1300 of the second embodiment of the orthopedic stabilization device 1010 does not have enlarged end portions to assist with retention. Instead, the passage of the suture 1400 through the openings 1314 and 1316 retains the locking member 1300 within the elongated loop opening 1106 of the depending loop 1104, thereby providing a retained orientation of the locking member 1300.

Figure 8A:
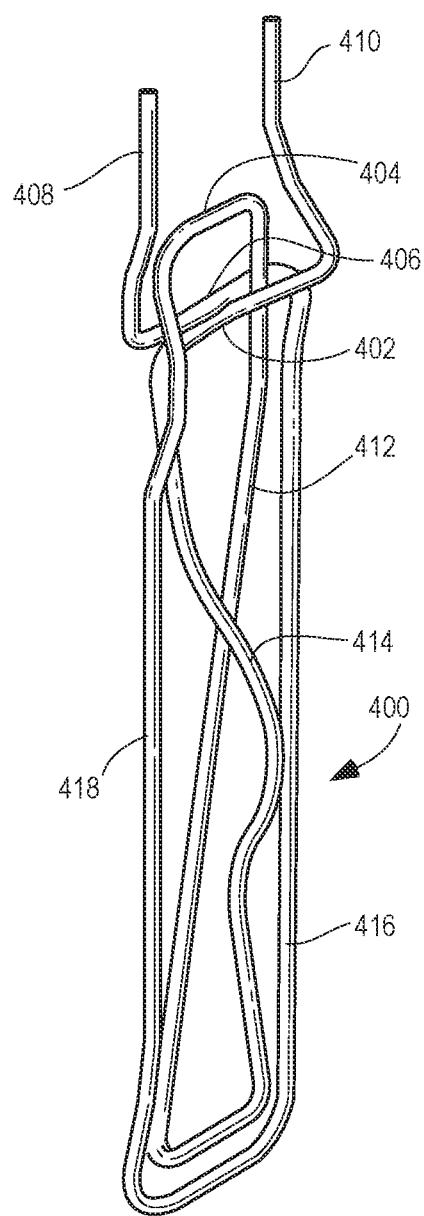
FIG. 8A depicts the suture of the orthopedic stabilization device of FIG. 1 with the first button, second button and locking member omitted to show the pattern of the suture.
Figure 8B:
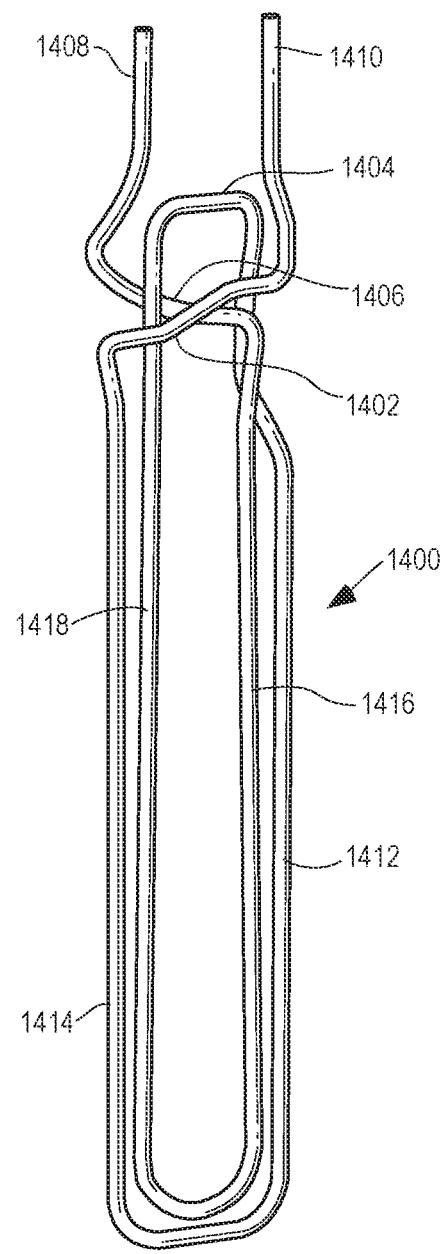
FIG. 8B depicts an alternative pattern of a suture suitable for use with the orthopedic stabilization device of FIG. 1.

Another difference is the threading pattern for the suture 1400 is like that of FIG. 8B, although the threading pattern shown in FIG. 8A can be equally suitable. The suture 1400 has a first segment 402 that extends through the elongated loop opening 1106 on an opposite side of the locking member 1300 relative to the base portion of the first button 1100. The suture 1400 also has a second segment 1404 that extends through the elongated loop opening 1106 on an adjacent side of the locking member 1300 relative to the base portion of the first button 1100. The suture 1400 also has a third segment 1406 extends that through the elongated loop opening 1106 on an opposite side of the locking member 1300 relative to the base portion 1102 of the first button 1100. The suture 1400 also has a pair of free ends 1408, 1410.

The suture 1400 is arranged in a pattern such that tensioning the free ends 1408, 1410 causes the second segment 1404 of the suture 1400 to pull the locking member 1300 toward the curved, distal end 1114 of the loop 1104 and away from the base 1102 of the first button 1100 to move the locking member 1300 toward the clamping position and clamp the first and third segments 1402, 1406 of the suture 1400 between a mid-section of the locking member 1300 and an interior side of the distal end 1114 of the loop 1104 within the enlarged loop opening 1106. With the first and third segments 1402, 1406 of the suture 1400 so clamped, the suture 1400 is restricted or prevented from movement that would allow the first button 1100 and the second button 1200 to move further apart. In other words, the distance between the first button 1100 and second button 1200 is restricted or fixed against increasing.

The suture 1400 can be arranged in a pattern, as shown in FIGS. 8B and 13-15, that extends through each of the two first button openings 1126, 1128, each of the two second button openings 1202, 1204 and each of the two locking member openings 1314, 1316. More specifically, and starting with a first 1408 of the free ends 1408, 1410 of the suture 1400, the suture 1400 extends through a first 1126 of the first button openings 1126, 1128, under the locking member 1300 and through the elongated loop opening 1106—defining the first segment 1402 of the suture 1400—and then through a first 1202 of the second button openings 1202, 1204 to a side of the second button 1200 opposite the first button 1100. The suture 1400 then extends through a second 1204 of the second button openings 1202, 1204 and through a second 1316 of the locking member openings 1314, 1316 to a side of the locking member 1300 facing the base portion 1102 of the first button 1100, through the elongated loop opening 1106 of the first button 1100 and then through a first 1314 of the locking member openings 1314, 1316, thereby defining the second segment 1404 of the suture 1400 extending between the locking member openings 1314, 1316 on a side of the locking member 1300 facing the base portion of the first button 1100. The suture 1400 then extends through the first 1202 of the second button openings 1202, 1204 to the opposite side of the second button 1200, then through the second 1204 of the second button openings 1202, 1204 and through the elongated loop opening 1106 between the locking member 1300 and the distal end 1114 of the loop 1104, and then through a second 1128 of the first button openings 1126, 1128. This results in a pattern where the suture 1400 has four strands 1412, 1414, 1416, 1418 extending between the first button 1100 and the second button 1200. Preferably, though not necessarily, there are only four strands 1412, 1414, 1416, 1418 or, alternatively, no more than four strands. As shown in FIGS. 8B and 13-15, there are two lateral strands 1412, 1414 and a pair of non-crossing intermediate strands 1416, 1418.

Figure 13:
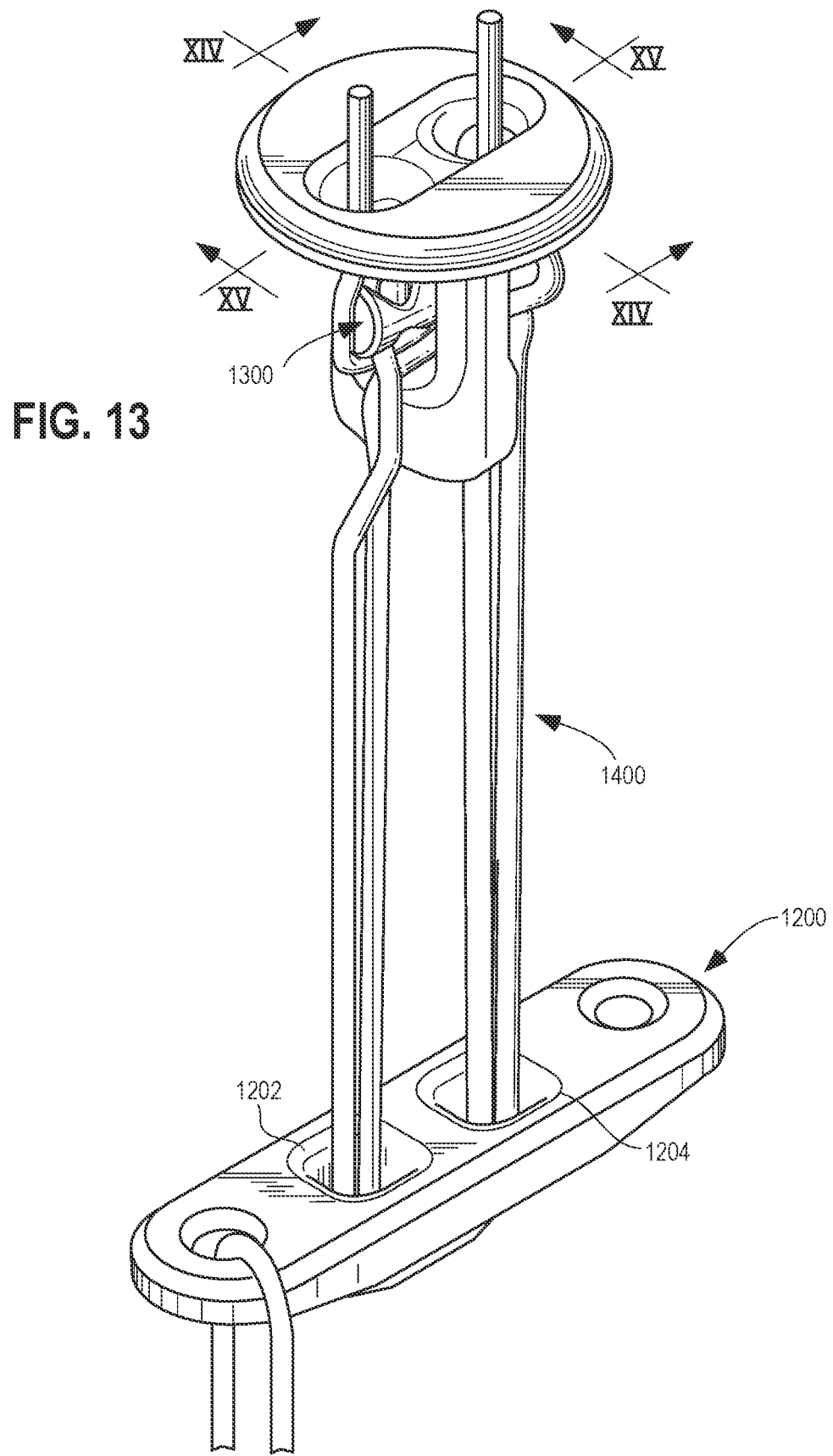
FIG. 13 is a perspective view of a second embodiment of an orthopedic stabilization device having a first button with a base and a depending loop, an alternative locking member extending through an elongated opening of the loop, a second button and a suture extending between the first and second buttons.
Figure 14:
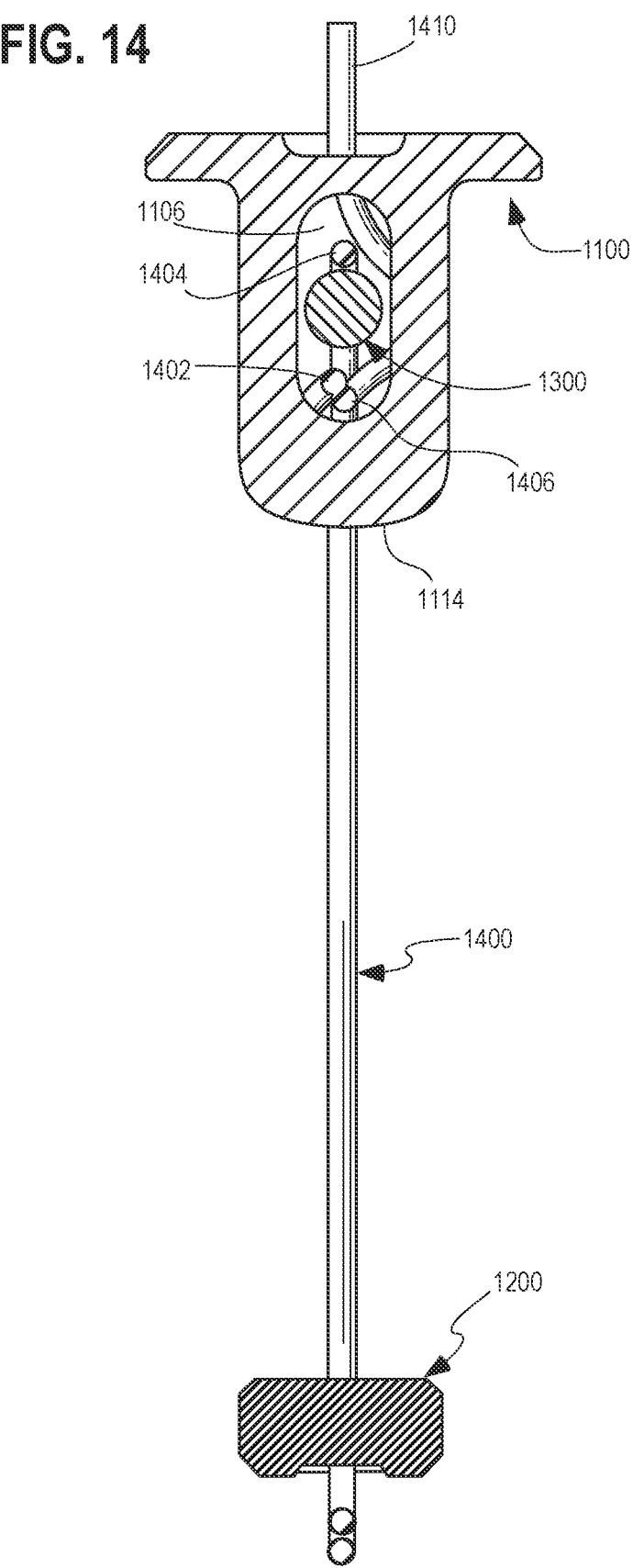
FIG. 14 is a cross-sectional view of the orthopedic stabilization device of FIG. 13 taken along line XIV-XIV thereof.
Figure 15:
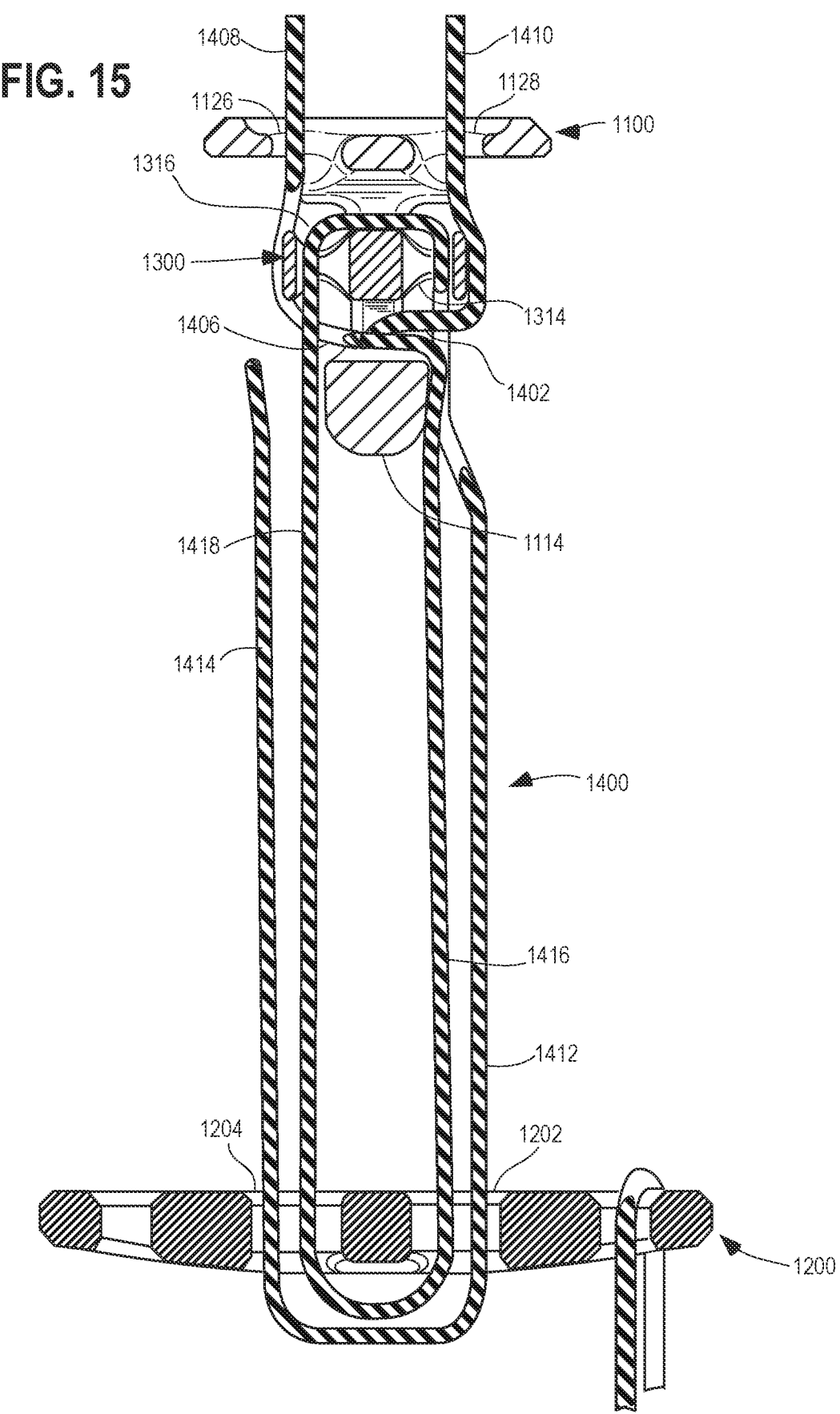
FIG. 15 is a cross-sectional view of the orthopedic stabilization device of FIG. 13 taken along line XV-XV thereof.
Figure 16A:
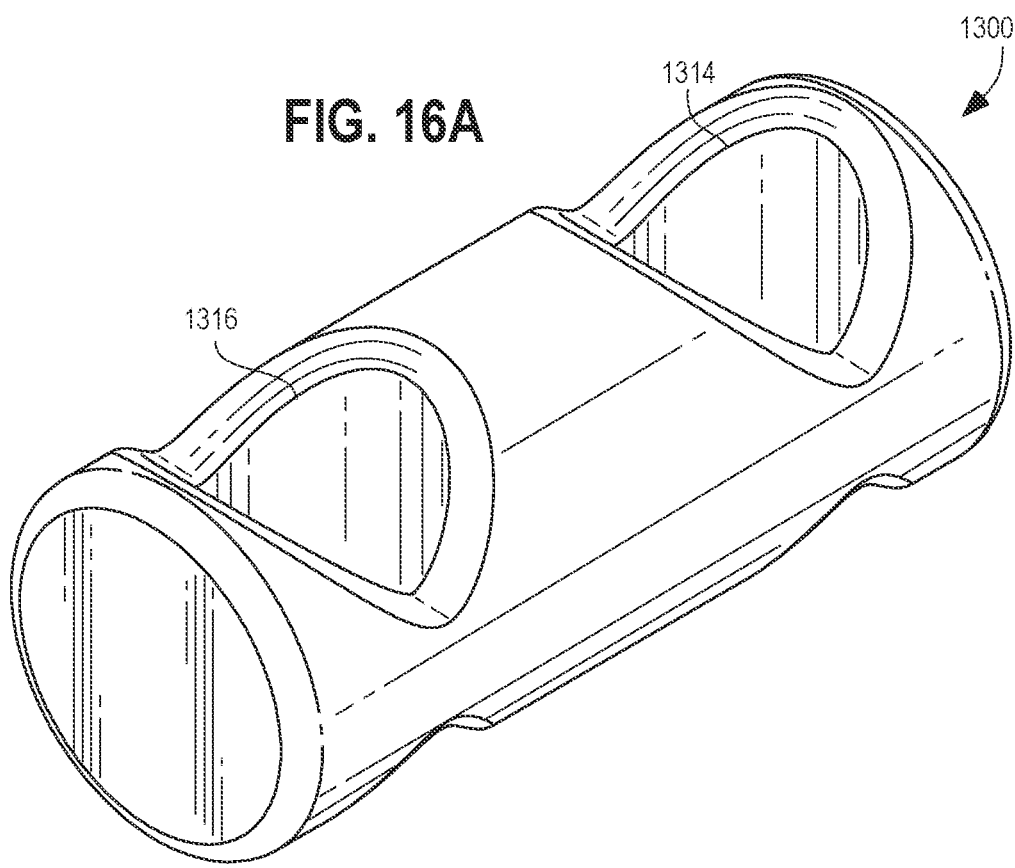
FIG. 16A is a perspective view of the alternative locking member of the orthopedic stabilization device of FIG. 13.
Figure 16B:
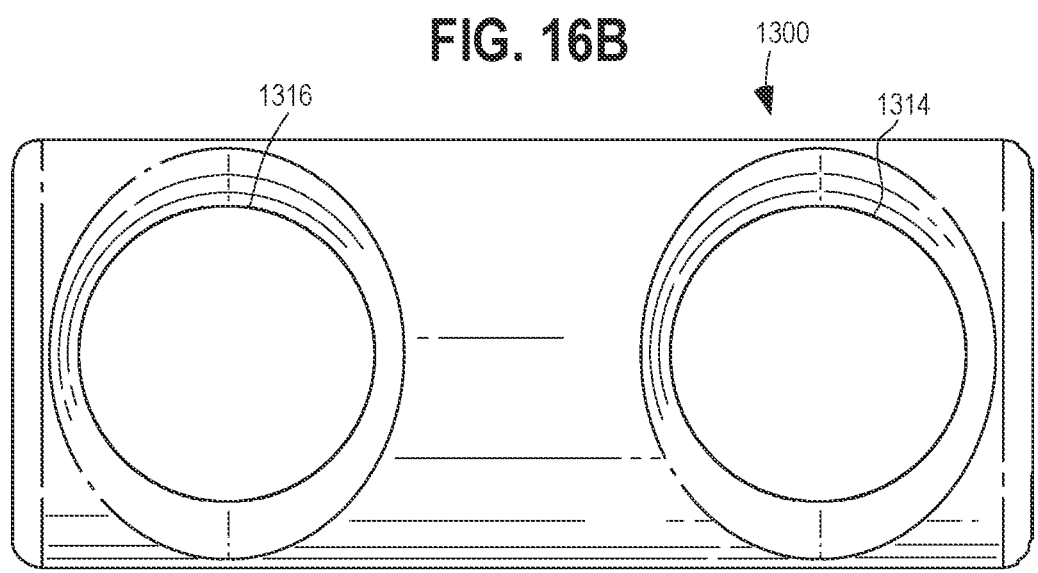
FIG. 16B is a top plan view of the locking member of FIG. 16A.

Another difference is the second button 1200 has additional features to facilitation deployment. Specifically, the second button 1200 has one or, as shown two through openings outwardly of the first and second button openings 1202 and 1204, as shown in FIGS. 13 and 15. A suture or thread can be inserted through one of the openings to assist with pulling the second button 1200 through a bore in a bone.

Although the locking members 300 and 1300 described above have locking member openings 314/316 and 1314/1316, such openings may be omitted. More specifically, another alternative locking member 2300, depicted in FIGS. 17A and 17B, has a shape somewhat similar to that of FIGS. 5A and 5B, but the openings 314/316 are omitted.

Figure 17A:
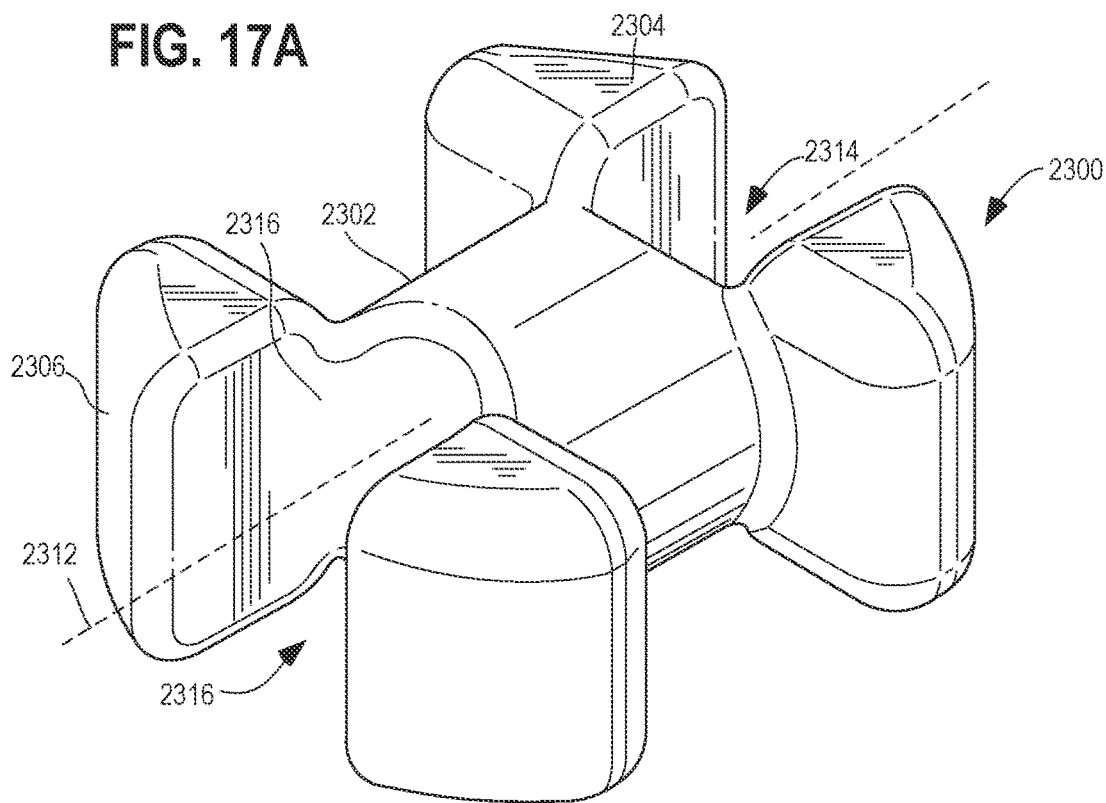
FIG. 17A is a perspective view of another alternative locking member suitable for use with the orthopedic stabilizations devices of any of the figures or as described herein.
Figure 17B:
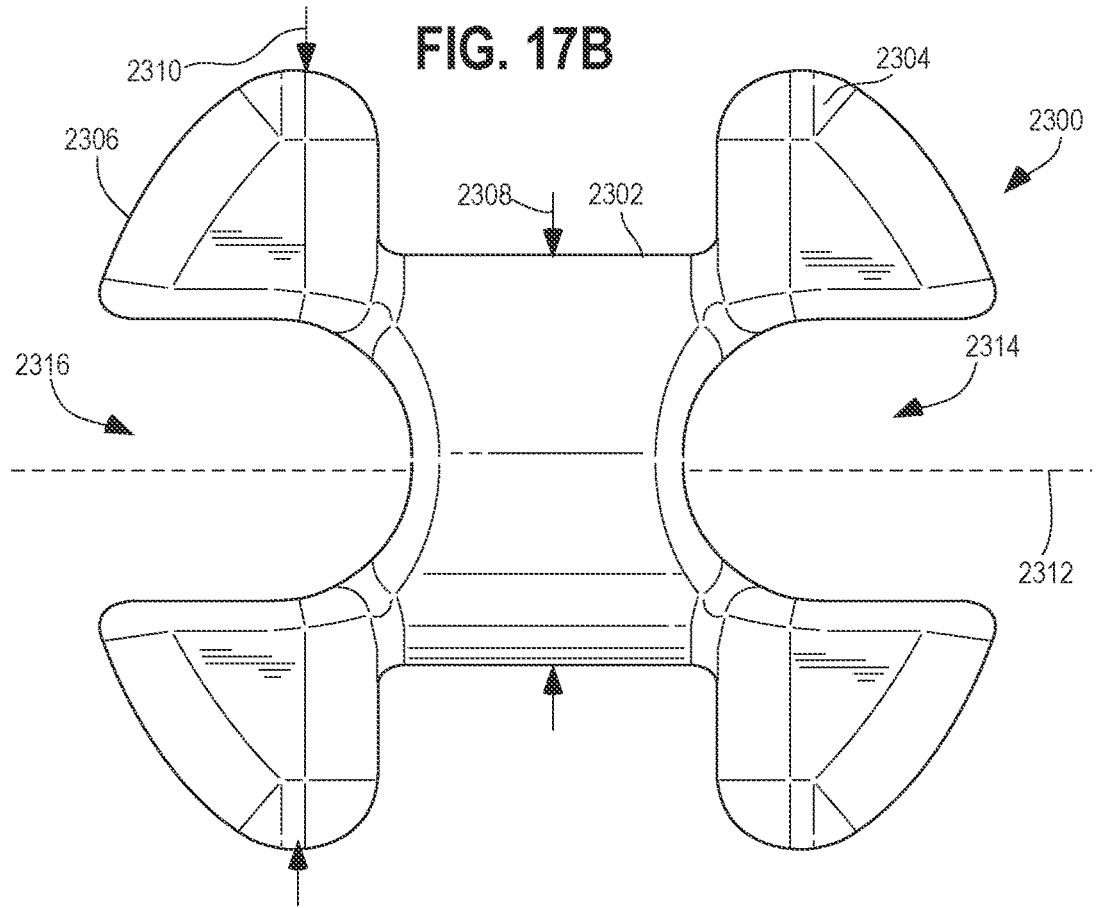
FIG. 17B is a top plan view of the locking member of FIG. 17A.

The locking member 2300 of FIGS. 17A and 17B is generally a flattened dumbbell shaped, with a narrow portion 2302 disposed between a pair of enlarged end portions 2304, 2306. The narrow portion 2302 is dimensioned to be slidingly disposed in the elongated loop opening 106/1106 of the first button 100/1000 when assembled. For example, the narrow portion 2302 can have a narrow dimension 2308 that is less than the minor dimension 124 of the elongated loop opening 106/1106 of the loop 104/1104 of the first button 100/1100. The enlarged end portions 2304, 2306 each have a maximum locking member dimension 2310 larger than the minor dimension 124 but yet smaller than the major dimension 122.

When in a first orientation, the enlarged end portions 2304, 2306 maintain the narrow portion 2302 in the elongated loop opening 106/1106 when aligned with the minor dimension 124. However, when rotated about a locking member axis 2312 until aligned with the major dimension 122 the enlarged end portions 2304, 2306 are able to pass through the elongated loop opening 106/1106. These dimensions 122, 124, 2308, 2310 allow the locking member 2300 to be readily assembled by inserting the locking member 2300 through the elongated loop opening 106/1106, but then retained once the locking member 2300 is rotated about the locking member axis 2312. Instead of openings, arcuate recesses 2314, 2316 receive the suture 400/1400 and optionally may cooperate with the suture 400/1400 to maintain the locking member 2300 laterally positioned within the loop 104/1104.

The invention claimed is:
1. An orthopedic stabilization device comprising:
a first button having a base portion and a depending loop, the base portion having two first button openings extending therethrough, and the loop having an elongated loop opening therethrough, the elongated loop opening having a major dimension and a minor dimension, the minor dimension being smaller than the major dimension;
a locking member slidably engaged with the loop of the first button, the locking member having a narrow portion disposed between a pair of enlarged end portions, the narrow portion being slidingly disposed in the elongated loop opening of the first button and the enlarged end portions each having a maximum width larger than the minor dimension and smaller than the major dimension such that the enlarged end portions maintain the narrow portion in the elongated loop opening when aligned with the minor dimension and allowing the locking member to disengage from the elongated loop opening when aligned with the major dimension;
a second button having two second button openings extending therethrough; and
a suture extending between the first button and the second button, with a portion of the suture being frictionally retainable between the locking member and the loop to thereby tie the first button to the second button.

2. The orthopedic stabilization device of claim 1, wherein the suture extends through each of the two first button openings and each of the two second button openings.

3. The orthopedic stabilization device of claim 2, wherein at least a first segment of the suture extends through the elongated loop opening on an opposite side of the locking member relative to the base portion.

4. The orthopedic stabilization device of claim 3, wherein a second segment of the suture extends through the elongated loop opening on an adjacent side of the locking member relative to the base portion.

5. The orthopedic stabilization device of claim 4, wherein each of the enlarged end portions has a locking member opening extending therethrough and the suture extends through each of the locking member openings.

6. The orthopedic stabilization device of claim 5, wherein the suture extends through each of the two second button openings twice.

7. The orthopedic stabilization device of claim 6, wherein the suture has no more than four strands extending between the first and second buttons.

8. The orthopedic stabilization device of claim 1, wherein each of the enlarged end portions has a locking member opening extending therethrough and the suture extends through each of the locking member openings.

9. The orthopedic stabilization device of claim 1, wherein the locking member has a clamping position wherein the portion of the suture frictionally retainable between the locking member and the loop is clamped between the locking member and the loop on an opposite side of the locking member relative to the base portion.

10. The orthopedic stabilization device of claim 9, wherein the suture has free ends on an opposite side of the base portion of the first button relative to the loop, and wherein tension applied on the free ends of the suture moves the locking member toward the clamping position.

11. The orthopedic stabilization device of claim 10, wherein each of the enlarged end portions has a locking member opening extending therethrough and the suture extends through each of the locking member openings, the two first button openings and the two second button openings.

12. The orthopedic stabilization device of claim 11, wherein the suture has no more than four strands that extend between the first button and the second button.

13. A method of using the orthopedic stabilization device of claim 10 comprising applying tension on the free ends of the suture to move the locking member into the clamping position.

14. A method of using the orthopedic stabilization device of claim 11 comprising applying tension on the free ends of the suture to move the locking member into the clamping position.

15. An orthopedic stabilization device comprising:
a first button having a base portion and a depending loop, the base portion having at least one first button opening extending therethrough, and the loop having an elongated loop opening therethrough;
a locking member extending through the elongated loop opening and having a clamping position and an unclamping position, the locking member being rotatable within the elongated loop opening between a retained orientation, whereby the locking member can slide within the elongated loop opening but not out of the elongated loop opening, and an unretained orientation where the locking member can be inserted into or removed from the elongated loop opening;
a second button having at least one second button opening extending therethrough; and
a suture extending between the first button and the second button and through the at least one first button opening and the at least one second button opening, with a portion of the suture being frictionally retainable between the locking member and the loop to thereby tie the first button to the second button when the locking member is in the clamping position to clamp the portion of the suture between the locking member and the loop on an opposite side of the locking member relative to the base portion.

16. An orthopedic stabilization device comprising:
a first button having a base portion and a depending loop, the base portion having two first button openings extending therethrough, and the loop having an elongated loop opening therethrough;
a locking member extending through the elongated loop opening and slidably engaged with the loop of the first button, the locking member having two locking member openings extending therethrough;
a second button having two second button openings extending therethrough; and
a suture extending between the first button and the second button, with a portion of the suture being frictionally retainable between the locking member and the loop to thereby tie the first button to the second button, wherein the suture extends through each of the two first button openings, each of the two second button openings, and each of the two locking member openings.

17. The orthopedic stabilization device of claim 16, wherein a first segment and a second segment of the suture extends through the elongated loop opening on an opposite side of the locking member relative to the base portion.

18. The orthopedic stabilization device of claim 17, wherein the second segment of the suture extends through the elongated loop opening on an adjacent side of the locking member relative to the base portion.

19. The orthopedic stabilization device of claim 17, wherein the locking member has a clamping position wherein the portion of the suture frictionally retainable between the locking member and the loop is clamped between the locking member and the loop on the opposite side of the locking member relative to the base portion, and wherein the suture has free ends on an opposite side of the base portion of the first button relative to the loop, and wherein tension applied on the free ends of the suture moves the locking member toward the clamping position.

20. A method of using the orthopedic stabilization device of claim 19 comprising applying tension on the free ends of the suture to move the locking member into the clamping position to clamp the first segment and the second segment of the suture between the locking member and the loop.

* * * * *